US011464923B2

(12) United States Patent
Liu et al.

(10) Patent No.: US 11,464,923 B2
(45) Date of Patent: Oct. 11, 2022

(54) INHALER SYSTEM

(71) Applicant: Norton (Waterford) Limited, Waterford (IE)

(72) Inventors: Xinyu Liu, Winchester, MA (US); Jenna-Leigh Meola, Cambridge, MA (US); Cody Goldberg, Cambridge, MA (US); Jinn Kim, Cambridge, MA (US); Sunil Kumar Mishra, Cambridge, MA (US); Vered Ben-Anat, Cambridge, MA (US)

(73) Assignee: Norton (Waterford) Limited, Waterford (IE)

( * ) Notice: Subject to any disclaimer, the term of this patent is extended or adjusted under 35 U.S.C. 154(b) by 0 days.

(21) Appl. No.: 16/906,896

(22) Filed: Jun. 19, 2020

(65) Prior Publication Data

US 2021/0393893 A1 Dec. 23, 2021

(51) Int. Cl.
*A61M 15/00* (2006.01)
*A61M 11/02* (2006.01)
(Continued)

(52) U.S. Cl.
CPC ....... *A61M 15/0001* (2014.02); *A61B 5/0871* (2013.01); *A61B 5/4833* (2013.01);
(Continued)

(58) Field of Classification Search
CPC .......... A61M 15/0001; A61M 15/0026; A61M 15/009; A61M 2202/064;
(Continued)

(56) References Cited

U.S. PATENT DOCUMENTS

| 5,941,241 A | * | 8/1999 | Weinstein | ............... A61F 17/00 |
| | | | | 128/200.14 |
| 6,571,790 B1 | * | 6/2003 | Weinstein | ............... A61F 17/00 |
| | | | | 128/200.14 |

(Continued)

FOREIGN PATENT DOCUMENTS

| EP | 1992381 A1 | 11/2008 |
| WO | 2018160073 A1 | 9/2018 |

(Continued)

OTHER PUBLICATIONS

"Bluetooth Pairing Part 4: Bluetooth Low EnergySecure Connections-Numeric Comparison", Bluetooth Technology Website; retrieved from https://www.bluetooth.com/blog/bluetooth-pairing-part-4, Jan. 19, 2017, 6 pages.

(Continued)

*Primary Examiner* — Tu A Vo
(74) *Attorney, Agent, or Firm* — Flaster Greenberg, P.C.

(57) ABSTRACT

Provided is a system including a plurality of inhalers that each include a processor configured to determine a value of a usage parameter relating to use of the respective first inhaler, encrypt data based on the value, and transmit the encrypted data. At least two of the inhalers include different medicament, such as a rescue medicament and a maintenance medicament. The system includes an external device that includes a processor configured to distinguish between the encrypted data of each respective inhaler, determine respective usage information relating to each of the distinct types of medicament based on the respective encrypted data, and control a user interface (e.g., of the external device) to communicate the usage information related to each inhaler and/or each respective type of medicament.

20 Claims, 12 Drawing Sheets

(51) Int. Cl.

| | |
|---|---|
| *G16H 40/67* | (2018.01) |
| *A61B 5/087* | (2006.01) |
| *G16H 20/13* | (2018.01) |
| *G06F 21/60* | (2013.01) |
| *G06K 7/14* | (2006.01) |
| *H04L 9/40* | (2022.01) |
| *A61B 5/00* | (2006.01) |
| *A61M 11/00* | (2006.01) |
| *A61M 16/00* | (2006.01) |

(52) U.S. Cl.
CPC .......... *A61B 5/7246* (2013.01); *A61B 5/7435* (2013.01); *A61M 11/02* (2013.01); *G06F 21/602* (2013.01); *G06K 7/1417* (2013.01); *G16H 20/13* (2018.01); *H04L 63/0428* (2013.01); *A61M 11/00* (2013.01); *A61M 15/003* (2014.02); *A61M 15/008* (2014.02); *A61M 15/009* (2013.01); *A61M 15/0026* (2014.02); *A61M 16/024* (2017.08); *A61M 2016/0027* (2013.01); *A61M 2202/064* (2013.01); *A61M 2205/18* (2013.01); *A61M 2205/27* (2013.01); *A61M 2205/3306* (2013.01); *A61M 2205/3358* (2013.01); *A61M 2205/3368* (2013.01); *A61M 2205/3375* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/6018* (2013.01); *A61M 2205/6072* (2013.01); *G16H 40/67* (2018.01)

(58) Field of Classification Search
CPC .... A61M 2205/3584; A61M 2205/502; A61M 2205/52; A61M 11/00–08; A61M 15/00–085; G16H 20/13; G06F 21/602; G06K 7/1417; H04L 63/0428
See application file for complete search history.

(56) References Cited

U.S. PATENT DOCUMENTS

| | | | | |
|---|---|---|---|---|
| 7,156,089 | B2* | 1/2007 | Weinstein | A61M 15/009 128/200.19 |
| 9,295,793 | B2 | 3/2016 | O'Hara et al. | |
| 9,364,619 | B2 | 6/2016 | Polidoro et al. | |
| 9,474,871 | B2 | 10/2016 | Feriani et al. | |
| 9,555,201 | B2 | 1/2017 | Collins et al. | |
| 9,706,946 | B2 | 7/2017 | Brimer et al. | |
| 10,089,055 | B1* | 10/2018 | Fryman | G09G 5/12 |
| 10,155,094 | B2 | 12/2018 | Wachtel et al. | |
| 10,220,166 | B2 | 3/2019 | Van Sickle et al. | |
| 10,258,753 | B2 | 4/2019 | Adams et al. | |
| 10,369,305 | B2 | 8/2019 | Li et al. | |
| 10,391,270 | B2 | 8/2019 | Adams et al. | |
| 2004/0172162 | A1* | 9/2004 | Bonney | A61M 15/0043 700/237 |
| 2005/0166913 | A1* | 8/2005 | Sexton | A61M 15/0065 128/200.14 |
| 2008/0308101 | A1* | 12/2008 | Spandorfer | A61M 15/008 128/203.14 |
| 2009/0314292 | A1* | 12/2009 | Overfield | A61B 5/087 128/203.15 |
| 2010/0094099 | A1* | 4/2010 | Levy | G16H 20/10 600/300 |
| 2010/0250280 | A1* | 9/2010 | Sutherland | A61M 15/009 705/3 |
| 2012/0048269 | A1 | 3/2012 | Pardonge et al. | |
| 2015/0136158 | A1* | 5/2015 | Stevens | A24F 47/00 131/329 |
| 2015/0257447 | A1* | 9/2015 | Sullivan | A61M 15/0086 131/329 |
| 2016/0129182 | A1* | 5/2016 | Schuster | G16H 40/63 702/56 |
| 2016/0144141 | A1 | 5/2016 | Sabharwal et al. | |
| 2016/0157524 | A1* | 6/2016 | Bowen | H05B 1/0244 128/200.14 |
| 2016/0325055 | A1* | 11/2016 | Cameron | A61M 11/005 |
| 2016/0330999 | A1* | 11/2016 | Cameron | A24F 40/30 |
| 2016/0331023 | A1* | 11/2016 | Cameron | A61M 11/042 |
| 2016/0331026 | A1* | 11/2016 | Cameron | A24F 40/40 |
| 2016/0331027 | A1* | 11/2016 | Cameron | A24F 40/53 |
| 2016/0331036 | A1* | 11/2016 | Cameron | A61M 15/0003 |
| 2016/0337362 | A1* | 11/2016 | Cameron | A61M 15/0003 |
| 2017/0055588 | A1* | 3/2017 | Cameron | A24F 1/22 |
| 2017/0100550 | A1* | 4/2017 | Van De Laar | G09B 23/28 |
| 2017/0136193 | A1* | 5/2017 | Cameron | A24F 47/008 |
| 2017/0136194 | A1* | 5/2017 | Cameron | A24F 40/65 |
| 2017/0140125 | A1* | 5/2017 | Hogg | A61M 15/0001 |
| 2017/0181474 | A1* | 6/2017 | Cameron | A24B 15/167 |
| 2017/0181475 | A1* | 6/2017 | Cameron | A24F 40/65 |
| 2017/0182267 | A1* | 6/2017 | Cameron | A24F 40/51 |
| 2017/0325734 | A1 | 11/2017 | Sutherland et al. | |
| 2018/0085540 | A1 | 3/2018 | Dantsker et al. | |
| 2018/0126099 | A1* | 5/2018 | Verjus | A61M 15/0065 |
| 2018/0140786 | A1 | 5/2018 | Calderon Oliveras et al. | |
| 2018/0161530 | A1 | 6/2018 | Ganton et al. | |
| 2018/0236187 | A1 | 8/2018 | Jung et al. | |
| 2019/0001085 | A1 | 1/2019 | Cottenden et al. | |
| 2019/0015608 | A1 | 1/2019 | Glusker et al. | |
| 2019/0030262 | A1 | 1/2019 | Ziegler et al. | |
| 2019/0060590 | A1 | 2/2019 | Starr et al. | |
| 2019/0111220 | A1 | 4/2019 | Richardson et al. | |
| 2019/0151577 | A1 | 5/2019 | Jung et al. | |
| 2019/0158938 | A1* | 5/2019 | Bowen | A61M 16/0051 |
| 2019/0175847 | A1* | 6/2019 | Pocreva, III | A61M 15/0065 |
| 2019/0175850 | A1 | 6/2019 | Petit | |
| 2019/0189258 | A1* | 6/2019 | Barrett | A61M 15/008 |
| 2019/0205541 | A1* | 7/2019 | Zimny | G06F 21/575 |
| 2019/0262556 | A1* | 8/2019 | Ciancone | A61M 15/0086 |
| 2019/0298942 | A1 | 10/2019 | Koblenski et al. | |
| 2019/0307648 | A1 | 10/2019 | Bartos | |
| 2020/0001026 | A1 | 1/2020 | Starr et al. | |
| 2020/0022416 | A1* | 1/2020 | Alarcon | A24F 40/53 |
| 2020/0061314 | A1* | 2/2020 | Hatamian | A61M 15/0066 |
| 2020/0155773 | A1 | 5/2020 | Zipkes et al. | |
| 2020/0178616 | A1* | 6/2020 | Yu | A61M 15/0083 |
| 2020/0229508 | A1* | 7/2020 | Israel | A61B 5/4833 |
| 2020/0345588 | A1* | 11/2020 | Merrell | G16H 20/10 |
| 2020/0352249 | A1* | 11/2020 | Achtien | A61M 15/0066 |
| 2020/0376209 | A1 | 12/2020 | Mohammed et al. | |
| 2020/0384216 | A1 | 12/2020 | Eicher et al. | |

FOREIGN PATENT DOCUMENTS

| | | |
|---|---|---|
| WO | 2020182655 A1 | 9/2020 |
| WO | 2020225662 A1 | 11/2020 |

OTHER PUBLICATIONS

"Metered-dose inhaler", Wikipedia; retrieved from https://en.widipedia.org/w/index.php?title=Metered-doseinhaler&oldid=894356801, Apr. 27, 2020, 8 pages.

* cited by examiner

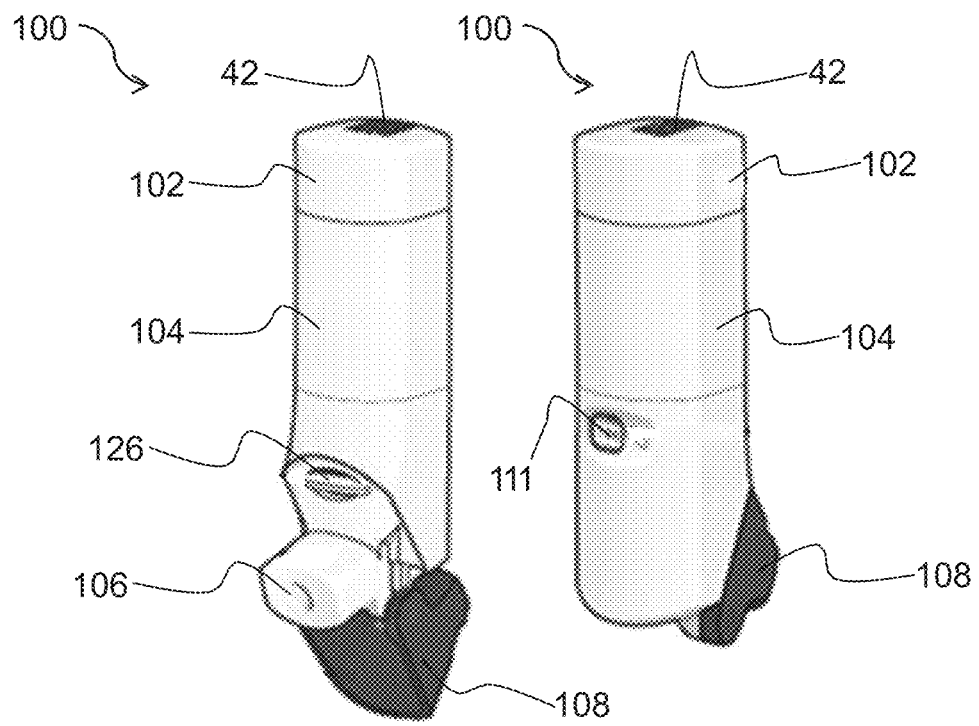
FIG. 4
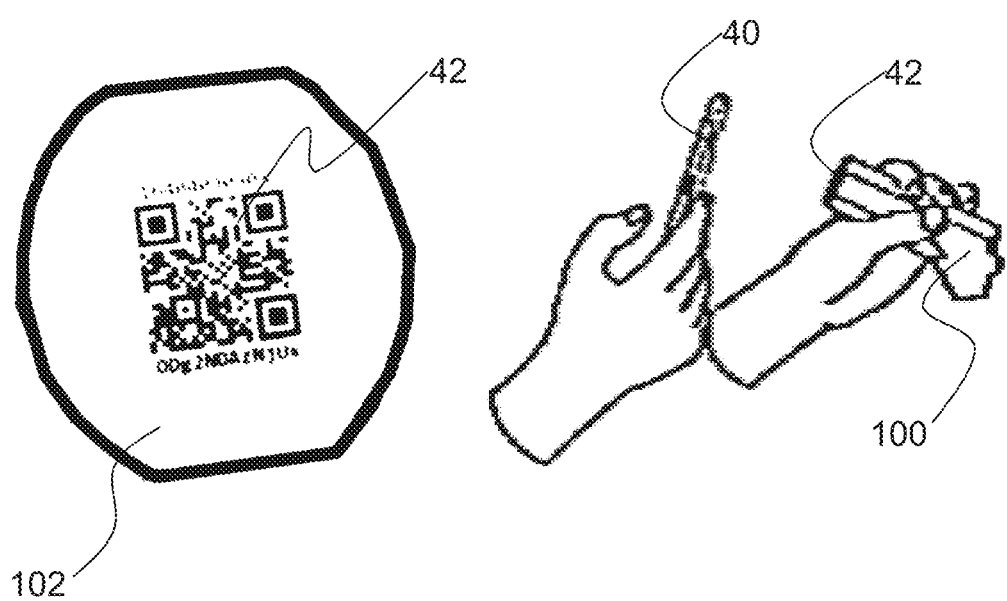
FIG. 5
FIG. 6

INHALER SYSTEM

TECHNICAL FIELD

This disclosure relates to an inhaler system, and particularly systems and methods for handling and communicating information relating to a subject's inhaler use.

BACKGROUND

Many respiratory diseases, such as asthma or chronic obstructive pulmonary disease (COPD), are life-long conditions where treatment involves the long-term administration of medicaments to manage the patients' symptoms and to decrease the risks of irreversible changes. There is currently no cure for diseases like asthma and COPD. Treatment takes two forms. First, a maintenance aspect of the treatment is intended to reduce airway inflammation and, consequently, control symptoms in the future. The maintenance therapy is typically provided by inhaled corticosteroids, alone or in combination with long-acting bronchodilators and/or muscarinic antagonists. Secondly, there is also a rescue (or reliever) aspect of the therapy, where patients are given rapid-acting bronchodilators to relieve acute episodes of wheezing, coughing, chest tightness and shortness of breath.

Sufferers of respiratory diseases may thus be prescribed more than one medication, such as more than one inhaled medication, for controlling their symptoms. The sufferer may alternatively or additionally make use of a plurality of inhalers, each being used at different times/locations, which all deliver the same inhaled medicament. There is a growing desire to monitor administration of such medicaments in ways which are reliable, and convenient from the point of view of the sufferer.

SUMMARY

Accordingly, the present disclosure provides a system for monitoring administration of medicaments. An example of such a system includes at least one first inhaler configured to deliver a first medicament to a subject. One or more (or each) of the at least one first inhaler includes a first use determination system. The first use determination system is configured to determine a first value of a usage parameter relating to use of the respective first inhaler. One or more (or each) of the at least one first inhaler includes a first transmission module. The first transmission module is configured to encrypt first data based on the first value. The first transmission module is configured to transmit the encrypted first data.

The exemplary system further includes at least one second inhaler. The at least one second inhaler is configured to deliver a second medicament to the subject. The second medicament is different from the first medicament. One or more (or each) of the at least one second inhaler includes a second use determination system. The second use determination system is configured to determine a second value of a usage parameter relating to use of the respective second inhaler. One or more (or each) of the at least one second inhaler includes a second transmission module. The second transmission module is configured to encrypt second data based on the second value. The second transmission module is configured to transmit the encrypted second data.

The exemplary system includes a user interface.

A processing module is also included in the exemplary system. The processing module is configured to receive the first encrypted data and the second encrypted data. The processing module is configured to distinguish between the first encrypted data and the second encrypted data. The processing module is configured to determine first usage information relating to the first medicament from the distinguished first encrypted data. The processing module is configured to determine second usage information relating to the second medicament from the distinguished second encrypted data. The processing module is configured to control the user interface to communicate the first and second usage information.

Thus, the processing module distinguishes between the first encrypted data and the second encrypted data. This allows the first encrypted data relating to administering of the first medicament to be processed separately from the second encrypted data relating to administering of the second medicament. As the first and second medicaments are different from each other, and thus may each be associated with distinct treatment regimens and/or administration protocols, this separate data processing may ensure that the first usage information relating to the first medicament does not become conflated with the second usage information relating to the second medicament. The system nevertheless permits consolidated handling and communicating of the first and second usage information.

BRIEF DESCRIPTION OF THE DRAWINGS

The embodiments will now be described in more detail with reference to the accompanying drawings, which are not intended to be limiting:

FIG. 4 shows front and rear views of the exterior of an inhaler according to an example;

FIG. 5 shows an uppermost surface of the top cap of the inhaler shown in FIG. 4;

FIG. 6 schematically depicts pairing the inhaler shown in FIG. 4 with a user device;

DETAILED DESCRIPTION

Figure 1:
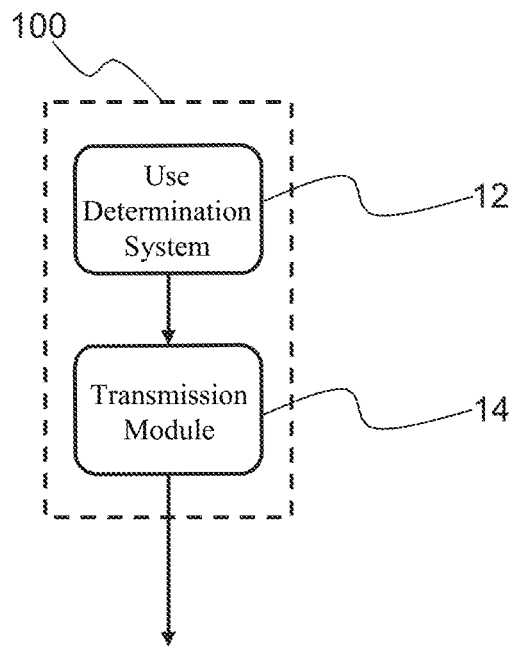
FIG. 1 shows a block diagram of an inhaler according to an example.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the figures to indicate the same or similar parts.

Asthma and COPD are chronic inflammatory disease of the airways. They are both characterized by variable and recurring symptoms of airflow obstruction and bronchospasm. The symptoms include episodes of wheezing, coughing, chest tightness and shortness of breath.

The symptoms are managed by avoiding triggers and by the use of medicaments, particularly inhaled medicaments. The medicaments include inhaled corticosteroids (ICSs) and bronchodilators.

Inhaled corticosteroids (ICSs) are steroid hormones used in the long-term control of respiratory disorders. They function by reducing the airway inflammation. Examples include budesonide, beclomethasone (dipropionate), fluticasone (propionate or furoate), mometasone (furoate), ciclesonide and dexamethasone (sodium). Parentheses indicate preferred salt or ester forms. Particular mention should be made of budesonide, beclomethasone and fluticasone, especially budesonide, beclomethasone dipropionate, fluticasone propionate and fluticasone furoate.

Different classes of bronchodilators target different receptors in the airways. Two commonly used classes are $\beta_2$-agonists and anticholinergics.

$\beta_2$-Adrenergic agonists (or "$\beta_2$-agonists") act upon the $\beta_2$-adrenoceptors which induces smooth muscle relaxation, resulting in dilation of the bronchial passages. They tend to be categorised by duration of action. Examples of long-acting $\beta_2$-agonists (LABAs) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). Examples of short-acting $\beta_2$-agonists (SABA) are albuterol (sulfate) and terbutaline (sulfate). Particular mention should be made of formoterol, salmeterol, indacaterol and vilanterol, especially formoterol fumarate, salmeterol xinafoate, indacaterol maleate and vilanterol triphenylacetate.

Typically short-acting bronchodilators provide a rapid relief from acute bronchoconstriction (and are often called "rescue" or "reliever" medicines), whereas long-acting bronchodilators help control and prevent longer-term symptoms. However, some rapid-onset long-acting bronchodilators may be used as rescue medicines, such as formoterol (fumarate). Thus, a rescue medicine provides relief from acute bronchoconstriction. The rescue medicine is taken as-needed/prn (pro re nata). The rescue medicine may also be in the form of a combination product, e.g. ICS-formoterol (fumarate), typically budesonide-formoterol (fumarate) or beclomethasone (dipropionate)-formoterol (fumarate). Thus, the rescue medicine is preferably a SABA or a rapid-acting LABA, more preferably albuterol (sulfate) or formoterol (fumarate), and most preferably albuterol (sulfate).

Anticholinergics (or "antimuscarinics") block the neurotransmitter acetylcholine by selectively blocking its receptor in nerve cells. On topical application, anticholinergics act predominantly on the $M_3$ muscarinic receptors located in the airways to produce smooth muscle relaxation, thus producing a bronchodilatory effect. Examples of long-acting muscarinic antagonists (LAMAs) include tiotropium (bromide), oxitropium (bromide), aclidinium (bromide), umeclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate) and darifenacin (hydrobromide). Particular mention should be made of tiotropium, aclidinium, umeclidinium and glycopyrronium, especially tiotropium bromide, aclidinium bromide, umeclidinium bromide and glycopyrronium bromide.

A number of approaches have been taken in preparing and formulating these medicaments for delivery by inhalation, such as via a dry powder inhaler (DPI), a pressurized metered dose inhaler (pMDI) or a nebulizer.

According to the GINA (global Initiative for Asthma) Guidelines, a step-wise approach is taken to the treatment of asthma. At step 1, which represents a mild form of asthma, the patient is given an as needed SABA, such as albuterol sulfate. The patient may also be given an as-needed low-dose ICS-formoterol, or a low-dose ICS whenever the SABA is taken. At step 2, a regular low-dose ICS is given alongside the SABA, or an as-needed low-dose ICS-formoterol. At step 3, a LABA is added. At step 4, the doses are increased and at step 5, further add-on treatments are included such as an anticholinergic or a low-dose oral corticosteroid. Thus, the respective steps may be regarded as treatment regimens, which regimens are each configured according to the degree of acute severity of the respiratory disease.

COPD is a leading cause of death worldwide. It is a heterogeneous long-term disease comprising chronic bronchitis, emphysema and also involving the small airways. The pathological changes occurring in patients with COPD are predominantly localised to the airways, lung parenchyma and pulmonary vasculature. Phenotypically, these changes reduce the healthy ability of the lungs to absorb and expel gases.

Bronchitis is characterised by long-term inflammation of the bronchi. Common symptoms may include wheezing, shortness of breath, cough and expectoration of sputum, all of which are highly uncomfortable and detrimental to the patient's quality of life. Emphysema is also related to long-term bronchial inflammation, wherein the inflammatory response results in a breakdown of lung tissue and progressive narrowing of the airways. In time, the lung tissue loses its natural elasticity and becomes enlarged. As such, the efficacy with which gases are exchanged is reduced and respired air is often trapped within the lung. This results in localised hypoxia, and reduces the volume of oxygen being delivered into the patient's bloodstream, per inhalation. Patients therefore experience shortness of breath and instances of breathing difficulty.

Patients living with COPD experience a variety, if not all, of these symptoms on a daily basis. Their severity will be determined by a range of factors but most commonly will be correlated to the progression of the disease. These symptoms, independent of their severity, are indicative of stable COPD and this disease state is maintained and managed through the administration of a variety drugs. The treatments are variable, but often include inhaled bronchodilators, anticholinergic agents, long-acting and short-acting $\beta_2$-agonists and corticosteroids. The medicaments are often administered as a single therapy or as combination treatments.

Patients are categorised by the severity of their COPD using categories defined in the GOLD Guidelines (Global Initiative for Chronic Obstructive Lung Disease, Inc.). The categories are labelled A-D and the recommended first choice of treatment varies by category. Patient group A are recommended a short-acting muscarinic antagonist (SAMA) prn or a short-acting $\beta_2$-aginist (SABA) prn. Patient group B are recommended a long-acting muscarinic antagonist (LAMA) or a long-acting $\beta_2$-aginist (LABA). Patient group C are recommended an inhaled corticosteroid (ICS)+a LABA, or a LAMA. Patient group D are recommended an ICS+a LABA and/or a LAMA.

Patients suffering from respiratory diseases like asthma or COPD suffer from periodic exacerbations beyond the baseline day-to-day variations in their condition. An exacerbation is an acute worsening of respiratory symptoms that require additional therapy, i.e. a therapy going beyond their maintenance therapy.

For asthma, the additional therapy for a moderate exacerbation are repeated doses of SABA, oral corticosteroids and/or controlled flow oxygen (the latter of which requires hospitalization). A severe exacerbation adds an anticholinergic (typically ipratropium bromide), nebulized SABA or IV magnesium sulfate.

For COPD, the additional therapy for a moderate exacerbation are repeated doses of SABA, oral corticosteroids and/or antibiotics. A severe exacerbation adds controlled flow oxygen and/or respiratory support (both of which require hospitalization). An exacerbation within the meaning of the present disclosure includes both moderate and severe exacerbations.

Provided is a system comprising at least one first inhaler which delivers a first medicament to a subject. One or more (or each) of the at least one first inhaler comprises a first use determination system configured to determine a first value of a usage parameter relating to use of the respective first inhaler. One or more (or each) of the at least one inhaler also comprises a first transmission module configured to encrypt first data based on the first value, and transmit the encrypted first data. The system further comprises at least one second inhaler which delivers a second medicament to the subject. The second medicament is different from the first medicament. One or more (or each) of the at least one second inhaler comprises a second use determination system configured to determine a second value of a usage parameter relating to use of the respective second inhaler, and a second transmission module configured to encrypt second data based on the second value, and transmit the encrypted second data.

The system includes a user interface, and a processing module. The processing module receives the first encrypted data and the second encrypted data, and distinguishes between the first encrypted data and the second encrypted data. The processing module determines first usage information relating to the first medicament from the distinguished first encrypted data, and determines second usage information relating to the second medicament from the distinguished second encrypted data. The processing module controls the user interface to communicate the first and second usage information.

One or more (or each) of the at least one first inhaler is configured to deliver a first medicament to a subject. One or more (or each) of the at least one first inhaler may, for example, comprise a first medicament reservoir containing the first medicament.

The system also comprises at least one second inhaler. One or more (or each) of the at least one second inhaler is configured to deliver a second medicament to the subject. This may be, for example, the same subject to whom the first medicament is administered via the first inhaler. The first medicament is different from the second medicament. One or more (or each) of the at least one second inhaler may, for example, comprise a second medicament reservoir containing the second medicament.

In a non-limiting example, the first medicament is a rescue medicament for use by the subject as needed, and the second medicament is a maintenance medicament which is used by the subject according to a predetermined treatment regimen.

The rescue medicament is as defined hereinabove and is typically a SABA or a rapid-onset LABA, such as formoterol (fumarate). The rescue medicament may also be in the form of a combination product, e.g. ICS-formoterol (fumarate), typically budesonide-formoterol (fumarate) or beclomethasone (dipropionate)-formoterol (fumarate). Such an approach is termed "MART" (Maintenance And Rescue Therapy).

In a non-limiting example, the first medicament is albuterol (sulfate), and the second medicament is fluticasone (propionate or furoate), or salmeterol (xinafoate) combined with fluticasone (propionate or furoate).

More generally, the first medicament and the second medicament (and any further medicaments included in any further inhalers included in the system) may comprise any suitable active pharmaceutical ingredient. Thus, any class of medication may be delivered by, in other words housed within, the inhalers included in the system. The system permits consolidated handling and communicating of usage information irrespective of the particular medications which are delivered by the inhalers.

One or more (or each) of the at least one first inhaler comprises a first use determination system. The first use determination system is configured to determine a first value of a usage parameter relating to use of the respective first inhaler. The usage parameter may, for instance, comprise a use of, such as an inhalation of the first medicament performed by the subject using, the respective first inhaler. Alternatively or additionally, the usage parameter may comprise a parameter relating to airflow during inhalation of the first medicament performed by the subject.

Similarly, one or more (or each) of the at least one second inhaler comprises a second use determination system. The second use determination system is configured to determine a second value of a usage parameter relating to use of the respective second inhaler. In the case of the second inhaler, the usage parameter may, for instance, comprise a use of, such as an inhalation of the second medicament performed by the subject using, the respective second inhaler. Alternatively or additionally, the usage parameter may comprise a parameter relating to airflow during inhalation of the second medicament performed by the subject.

One or more (or each) of the first inhaler comprises a first transmission module configured to encrypt first data based on the first value, and transmit the encrypted first data. Similarly, one or more (or each) of the second inhaler comprises a second transmission module configured to encrypt second data based on the second value, and transmit the encrypted second data.

The first and second transmission modules may each include an encryption device capable of encrypting the first and second data, respectively. For example, the encryption device may be implemented using hardware such a digital signal processor (DSP), a microcontroller, a processor, and/or the like. The encryption device may be incorporated into other portions of the first and/or second transmission modules, such as a transceiver use to transmit the encrypted data. Examples of different types of transceivers are described in more detail below.

The system comprises a processing module configured to receive the first encrypted data and the second encrypted data from the respective transmission modules.

The processing module may include a general purpose processor, a special purpose processor, a DSP, a microcontroller, an integrated circuit, and/or the like that may be configured using hardware and/or software to perform the functions described herein for the processing module. The processing module may include a power supply and/or a battery.

Encryption of the first and second data in this manner enables transmission of the respective usage parameter values. The encryption may, for instance, further enable such transmission to be effected securely, since decryption of the respective data is implemented by the processing module configured to receive the encrypted data from the respective transmission modules. The processing module may, for example, be paired to the respective transmission modules such that the processing module is configured, e.g. exclusively configured, to decrypt the encrypted data. Thus, such encryption may enable secure transmission of the respective usage parameter values to the processing module, which secure transmission may be preferred in the context of transmission of medical data relating to inhaler usage.

In a non-limiting example, the first and/or second transmission modules are configured to transmit the respective encrypted data wirelessly. A transceiver configured to implement any suitable wireless transmission protocol may be included in the respective transmission modules, such as via Wi-Fi, Wi-MAX, Bluetooth®, Bluetooth® Smart, ZigBee, near field communication (NFC), cellular communication, television white space (TVWS) communication, or any combination thereof.

Although examples described herein may refer to a transceiver, the transceiver may be configured to transmit, but not receive, data (e.g., a transmitter but not a receiver). The transceiver may include one or more semiconductor chips, integrated circuits, and/or the like configured to implement the logic and procedures of the communication protocol. The transceiver may include radio frequency (RF) hardware such as amplifier(s), oscillator(s), modulator circuit(s), antenna(s), antenna tuner(s), and/or the like in order to transmit signals wirelessly using the communication protocol. The RF hardware may be implemented in whole or in part on the semiconductor chip(s), integrated circuit(s), and/or the like configured to implement the logic and procedures of the communication protocol.

Preferably, the data is transmitted from the respective transmission modules to the processing module, and from the processing module to the respective transmission modules via Bluetooth®. Bluetooth® may be preferred because the relatively low energy associated with transmitting and receiving may preserve the battery life of the respective inhaler. Moreover, no internet connection need be established in order for the respective encrypted data to be transmitted to the processing module.

Whilst the respective transmission modules are configured to transmit the encrypted data, in some non-limiting examples the respective transmission modules are further configured to receive data, for example from the processing module to which the encrypted data is sent. In such examples, the respective transmission modules may be regarded as a transceiver, in other words as a transmitting and receiving module.

A clock module may, for example, be included in one or more (or each) of the respective inhalers for assigning a time, for example a time stamp, to the usage parameter of the respective inhaler. The clock module may be implemented via a processor or other type of integrated circuit. The processing module may be configured to synchronize the clock modules of the respective inhalers. One or more (or each) of the respective clock modules may, for instance, receive time data transmitted from the processing module, e.g. via the respective transmission module. Such synchronization may, for instance, provide a point of reference which enables the relative timing of use of the respective inhalers to be determined, which may have clinical relevance. For example, failure to inhale a maintenance medicament during a particular time period in which such an inhalation was or such inhalations were scheduled according to a treatment regimen may be correlated with increased rescue medicament usage towards the end of, or subsequently to, that time period of non-adherence to the treatment regimen. Such diagnostic analysis may be possible when the clock modules of the respective inhalers are synchronized with each other.

Further, it should be appreciated that in some examples, the clock module of an inhaler may operate as an internal counter. When operating as an internal counter, the clock module may provide a relative count (e.g., as opposed to providing a mean solar time, such as a local mean time). For instance, the use determination system of an inhaler may start an internal counter (e.g., which counts up from 0 indefinitely) when, for example, the use determination system is woken out of an energy-saving sleep mode for the first time (e.g., after the mouthpiece cover is opened for the first time). Thereafter, any time-and-date stamp generated by the use determination system may be a relative time (or count) based on the internal counter of the clock module. The use determination system may periodically update the system clock every 250 microseconds ($\mu s$).

The processing module may, in some examples, comprise a further clock module. The clock modules of each of the respective inhalers may thus be synchronized according to the time provided by the further clock module. The further clock module may, for instance, receive the time of the time zone in which the processing module is situated. The processing module may, for example, transmit the time of the time zone to the respective clock modules, thereby to permit the clock modules to be synchronized according to the time in which the subject and their respective inhalers are located. Time stamping of the respective usage information may thus correspond to the time of day or night at the subject's geographical location. This is particularly advantageous given the relevance of, for example, night time rescue medicament use to the risk of an impending respiratory disease exacerbation. The system may thus, for example, monitor the day time and night time rescue inhaler usage of a subject who has travelled across time zones. Alternatively or additionally, reminders issued by the system to remind the subject to administer a maintenance medicament may account for the time of day or night at the subject's location.

The processing module is configured to distinguish between the first encrypted data and the second encrypted data. First usage information relating to the first medicament is determined by the processing module based on the distinguished first encrypted data. Similarly, second usage information relating to the second medicament is determined by the processing module based on the distinguished second encrypted data.

In an embodiment, the processing module receives a first identifier assigned to the first medicament. In such an example, a second identifier is assigned to the second medicament. In such an example, the first identifier is not associated with or assigned to the second medicament and the second identifier is not associated with or assigned to the first medicament. The processing module receives the respective identifiers, and uses the respective identifiers to distinguish between the first encrypted data and the second encrypted data.

The respective identifier may, in certain examples, also denote further information, such as the dose strength of each dose delivered by the respective inhaler, for example via a suitable dose metering assembly included in the inhaler. Alternatively or additionally, the respective identifier may denote the total number of doses of the respective medicament contained by the respective inhaler (prior to first use), in other words in the medicament reservoir of the respective inhaler as supplied.

The processing module may, for instance, be accordingly configured to recognize the dose strength and/or the total number of doses which can be provided by the respective inhaler from the respective identifier. Moreover, when the respective identifier denotes the dose strength, the processing module may be configured to, for example, control the user interface to issue a notification that the label recommended dosages have been exceeded based on the respective usage information, in this case uses of the respective inhaler, and the respective dose strength.

In some examples in which a further inhaler configured for dispensing a medicament is added to the system which already includes an existing inhaler which dispenses the same medicament, the processing module may be configured to determine, based on the respective identifiers for the existing inhaler and the further inhaler whether the dose strength of the further inhaler is the same as or different from that of the existing inhaler. If the respective dose strengths are different from each other, the processing module controls a user interface to issue at least one notification. The at least one notification may, for example, comprise a notification informing the subject that the dose strength of the further inhaler is different from that of the existing inhaler and/or a notification to request that the subject discards the existing inhaler. In this manner, the system may assist the subject to adjust to a prescription change. The medicament in this example may be a rescue medicament or a maintenance medicament.

When the respective identifier denotes the total number of doses contained by the respective inhaler, the processing module may be configured to control the user interface to issue a notification that the respective inhaler should be replaced based on the respective usage information, in this case uses of the respective inhaler, and the respective total number of doses as denoted by the respective identifier. For instance, subtraction of the number of uses of the respective inhaler as determined via the use determination system from the total number of doses denoted by the respective identifier will provide the number of doses remaining in the respective inhaler. The notification may be triggered by the processing module when the determined number of doses remaining in the respective inhaler reaches or becomes lower than a predetermined threshold number of doses.

In a non-limiting example, the first identifier is included in a first key which is used to pair the first inhaler and the processing module. The processing module is configured to identify the first inhaler as an inhaler which delivers the first medicament on the basis of the first identifier included in the first key. Similarly, the second identifier may be included in a second key for pairing the second inhaler and the processing module, and the processing module identifies the second inhaler as an inhaler which delivers the second medicament on the basis of the second identifier included in the second key. In this manner, the first encrypted data is linked to the first medicament, and the second encrypted data is linked to the second medicament.

More generally, by the processing module distinguishing between the first encrypted data and the second encrypted data, the first encrypted data relating to administering of the first medicament is processed separately from the second encrypted data relating to administering of the second medicament. Because the first and second medicaments are different from each other, and thus may each be associated, for instance, with distinct treatment regimens and/or administration protocols, this separate data processing may advantageously ensure that the first usage information relating to the first medicament does not become conflated with the second usage information relating to the second medicament. The system nevertheless permits consolidated handling and communicating of the first and second usage information.

The processing module is configured to control the user interface to communicate, for example display, the first and second usage information. In this way, the subject is informed of their usage of the first and second medicaments respectively. In the case of the first or second medicament being, for instance, a rescue medicament, the system may enable the subject to track the status of their respiratory disease. In the case of the first or second medicament being, for example, a maintenance medicament, the system may enable the subject to track their adherence to, or compliance with, a predetermined treatment regimen. In some examples, the processing module is configured to control the user interface to display the first and second usage information simultaneously, such as in a single graphical user interface (GUI).

In an embodiment, the system further comprises at least one third inhaler. One or more (or each) of the at least one third inhaler is configured to deliver a third medicament to the subject. This may be, for example, the same subject to whom the first and second medicaments are administered via the first inhaler and the second inhaler respectively. The third medicament is different from the first and second medicaments. One or more (or each) of the at least one third inhaler may, for example, comprise a third medicament reservoir containing the third medicament.

One or more (or each) of the at least one third inhaler comprises a third use determination system configured to determine a third value of a usage parameter relating to use of the respective third inhaler. The usage parameter may, for instance, comprise a use of, such as an inhalation of the third medicament performed by the subject using, the respective third inhaler. Alternatively or additionally, the usage parameter may comprise a parameter relating to airflow during inhalation of the third medicament performed by the subject.

In a non-limiting example, the first medicament is a rescue medicament for use by the subject as needed, the second medicament is a maintenance medicament which is used by the subject according to a predetermined treatment regimen, and the third medicament is a further maintenance medicament which is used by the subject according to a further predetermined treatment regimen.

In a non-limiting example, the first medicament is albuterol (sulfate), and the second medicament is salmeterol (xinafoate) combined with fluticasone (propionate or furoate), budesonide combined with formoterol (fumarate), or beclomethasone (dipropionate).

The third inhaler further comprises a third transmission module configured to encrypt third data based on the third value, and transmit the encrypted third data. The processing module is further configured to receive the third encrypted data, and distinguish the third encrypted data from the encrypted data transmitted from the respective transmission modules included in the other inhalers included in the system. The processing module determines third usage information relating to the third medicament from the distinguished third encrypted data.

The third transmission module may, for example, be configured to provide a third identifier assigned to the third medicament. In this example, the processing module is configured to receive the third identifier, and use the first, second, and third identifiers to distinguish the third encrypted data from the first and second encrypted data. The third identifier may, in certain examples, also denote further information, such as the dose strength and/or the total number of doses of the third medicament contained by the third inhaler, in other words in the third medicament reservoir of the third inhaler.

In a non-limiting example, the third identifier is included in a third key which is used to pair the third inhaler and the processing module. The processing module is configured to identify the third inhaler as an inhaler which delivers the third medicament on the basis of the third identifier included in the third key, as previously described in relation to the first and second inhalers.

More generally, the third encrypted data relating to administering of the third medicament is processed separately from the first and second encrypted data relating to administering of the first and second medicaments. Because the first, second, and third medicaments are different from each other, and thus may each be associated, for instance, with distinct treatment regimens and/or administration protocols, this separate data processing may advantageously ensure that the third usage information relating to the third medicament does not become conflated with the first and second usage information relating to the first and second medicaments. The system nevertheless permits consolidated handling of the first, second, and/or third usage information. In this respect, the processing module controls the user interface to communicate, for example display, the first, second, and/or third usage information.

In some non-limiting examples, the system comprises two or more first inhalers, such as two, three, four, five, or more first inhalers. Such a plurality of first inhalers may be particularly advantageous when, for example, the first medicament is a rescue medicament. In such an example, the subject may place first inhalers in various different locations, such as on a nightstand, in a gym bag, in a vehicle, and so on, in order that the rescue medicament is readily available if needed.

In other non-limiting examples, the first medicament is a maintenance medicament. In such an example, the subject may place first inhalers in various different locations in order to facilitate administration of the maintenance medicament at points during the subject's daily routine, thereby assisting the subject to adhere to the treatment regimen associated with the maintenance medicament.

In a non-limiting example, the first identifier is the same for all of the plurality of first inhalers. Whilst the plurality of first inhalers may, for instance, each have a first key which is different from the other first inhalers (and that of the second inhaler(s) and, when present, that of the third inhaler (s)), each of the first keys comprise the first identifier. In this way, the first encrypted data is linked to the first medicament irrespective of the fact that several first inhalers may be being used by the subject. The system thus permits tracking of use of the first medicament in spite of the latter being administered via a plurality of first inhalers.

Similar considerations are applicable to the at least one second inhaler, and, when present, the at least one third inhaler. In other words, the at least one second inhaler may comprise two or more second inhalers. Alternatively or additionally, the at least one third inhaler may comprise two or more third inhalers.

More generally, the system may, for example, comprise a fourth inhaler, a fifth inhaler, and so on. The first, second, third, fourth, fifth, etc. inhalers may dispense a different medicament from the others. In a non-limiting example, the respective medicaments are: albuterol; salmeterol combined with fluticasone; fluticasone; beclomethasone combined with albuterol; budesonide combined with formoterol.

In some non-limiting examples, at least one of the respective medicaments is a LAMA, such as those identified hereinabove.

Further provided is a method comprising receiving first encrypted data from a first transmission module of a first inhaler configured to deliver a first medicament to a subject. The first encrypted data is based on a first value of a usage parameter relating to use of the first inhaler, e.g. as determined by a first use determination system included in the first inhaler. The method also comprises receiving second encrypted data from a second transmission module included in a second inhaler configured to deliver a second medicament to the subject. The second encrypted data is based on a second value of a usage parameter relating to use of the second inhaler, e.g. as determined by a second use determination system included in the second inhaler. The second medicament is different from the first medicament. The first encrypted data and the second encrypted data are distinguished from each other. First usage information relating to the first medicament is determined from the distinguished first encrypted data. Second usage information relating to the second medicament is determined from the distinguished second encrypted data. The method further comprises controlling a user interface to communicate, for example display, the first and second usage information.

A computer program is also provided, which computer program comprises computer program code which is adapted, when the computer program is run on a computer, to implement the method.

The embodiments described herein for the system are applicable to the method and the computer program. Moreover, the embodiments described for the method and computer program are applicable to the system.

FIG. 1 shows a block diagram of an inhaler 100 according to an example. The inhaler 100 comprises a use determination system 12 which determines at least one value of a usage parameter. The at least one value of the usage parameter is received by a transmission module 14, as represented in FIG. 1 by the arrow between the block representing the use determination system 12 and the block representing the transmission module 14. The transmission module 14 encrypts data based on the value(s) of the usage parameter, and transmits the encrypted data, as represented in FIG. 1 by the arrow pointing away from the transmission module 14 block. The transmission of the encrypted data by the transmission module 14 may, for example, be wireless, as previously described.

The usage parameter may, for example, comprise a use of the respective inhaler. In a relatively simple implementation, the at least one value may comprise "TRUE" when use of, for example an inhalation using, the respective inhaler has been determined, or "FALSE" when no such use of the respective inhaler is determined.

The use determination system 12 may include one or more components used to determine at least one value of a usage parameter of inhaler 100. The usage parameter may be one or more of a count of the number of uses inhaler 100, a measure of airflow of inhaler 100, and/or other measurements indicating the usage of the medicament of inhaler 100. The use determination system 12 may include one or more of a switch configured to detect usage of inhaler 100, one or more sensors configured to detect use of inhaler 100, one or more buttons configured to be depressed upon use of inhaler 100, and/or the like.

For example, the use determination system 12 may, for instance, comprise a mechanical switch configured to be actuated prior to, during, or after use of the respective inhaler. The mechanical switch may indicate that a dose of medicament has been primed and is ready for inhalation (e.g., such as by metering a dose from a hopper, advancing and/or opening a blister pack, etc.). In a non-limiting example, the inhaler 100 comprises a medicament reservoir (not visible in FIG. 1), and a dose metering assembly (not visible in FIG. 1) configured to meter a dose of the rescue medicament from the reservoir.

The use determination system 12 may be configured to register the metering of the dose by the dose metering assembly, each metering being thereby indicative of the inhalation performed by the subject using the inhaler 100. Accordingly, the inhaler 100 may be configured to monitor the number of inhalations of the medicament, since the dose should be metered via the dose metering assembly before being inhaled by the subject. One non-limiting example of the dose metering assembly will be explained in greater detail with reference to FIGS. 12-16.

Alternatively or additionally, the use determination system 12 may register each inhalation in different manners and/or based on additional or alternative feedback. For example, the use determination system 12 is configured to register an inhalation by the subject when the feedback from a suitable sensor (not visible in FIG. 1) indicates that an inhalation by the subject has occurred, for example when a pressure measurement or flow rate exceeds a predefined threshold associated with a successful inhalation.

A sensor, such as a pressure sensor or acoustic sensor, may, for example, be included in the use determination system 12 in order to register each inhalation. Such a sensor may be an alternative or in addition to the abovementioned mechanical switch. When a pressure or acoustic sensor is included in the use determination system 12, the pressure sensor may, for instance, be used to confirm that, or assess the degree to which, a dose metered via the dose metering assembly is inhaled by the subject, as will be described in greater detail with reference to FIGS. 2 and 12-16.

More generally, the use determination system 12 may comprise a sensor for detecting a parameter relating to airflow during inhalation of the respective medicament performed by the subject. In other words, the usage parameter comprises a parameter relating to airflow during inhalation of the medicament. The at least one value may thus, for example, comprise a numerical value relating to the detected inhalation parameter.

The inhalation parameter may be, for example, at least one of a peak inhalation flow, an inhalation volume, a time to peak inhalation flow, and an inhalation duration. In such examples, the at least one value comprises a numerical value for the peak inhalation flow, the inhalation volume, the time to peak inhalation flow, and/or the inhalation duration.

A pressure sensor may be particularly suitable for measuring the parameter, since the airflow during inhalation by the subject may be monitored by measuring the associated pressure changes. As will be explained in greater detail with reference to FIGS. 12-16, the pressure sensor may be located within or placed in fluid communication with a flow pathway through which air and the medicament is drawn by the subject during inhalation. Alternative ways of measuring the parameter, such as via a suitable flow sensor, can also be used.

An inhalation may be associated with a decrease in the pressure in the airflow channel of the inhaler relative to when no inhalation is taking place. The point at which the pressure change is at its greatest may correspond to the peak inhalation flow. The pressure sensor may detect this point in the inhalation.

The pressure change associated with an inhalation may alternatively or additionally be used to determine an inhalation volume. This may be achieved by, for example, using the pressure change during the inhalation measured by the pressure sensor to first determine the flow rate over the time of the inhalation, from which the total inhaled volume may be derived.

The pressure change associated with an inhalation may alternatively or additionally be used to determine an inhalation duration. The time may be recorded, for example, from the first decrease in pressure measured by the pressure sensor, coinciding with the start of the inhalation, to the pressure returning to a pressure corresponding to no inhalation taking place.

The inhalation parameter may alternatively or additionally include the time to peak inhalation flow. This time to peak inhalation flow parameter may be recorded, for example, from the first decrease in pressure measured by the pressure sensor, coinciding with the start of the inhalation, to the pressure reaching a minimum value corresponding to peak flow.

Figure 2:
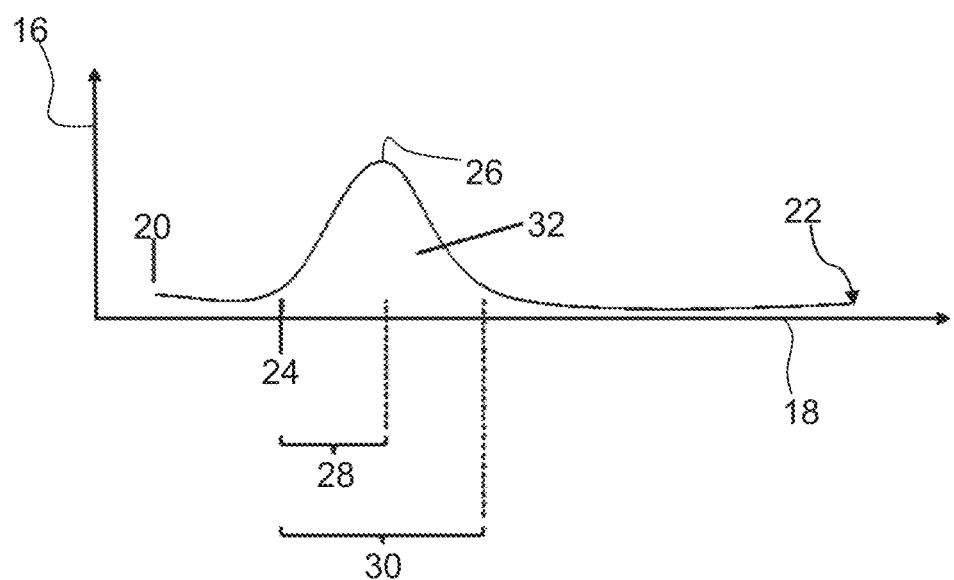
FIG. 2 shows a graph of flow rate versus time during use of an inhaler according to an example.

FIG. 2 shows a graph of flow rate 16 versus time 18 during use of an inhaler 100 according to a non-limiting example. The use determination system 12 in this example comprises a mechanically operated switch in the form of a switch which is actuated when a mouthpiece cover of the inhaler 100 is opened. The mouthpiece cover is opened at point 20 on the graph. In this example, the use determination system 12 further comprises a pressure sensor.

When the mouthpiece cover is opened, the use determination system 12 is woken out of an energy saving sleep mode, and a new inhalation event is registered. The inhalation event is also assigned an open time corresponding to how much time, for example milliseconds, elapses since the inhaler 100 wakes from the sleep mode. Point 22 corresponds to the cap closing or 60 seconds having elapsed since point 20. At point 22, detection ceases.

Once the mouthpiece cover is open, the use determination system 12 looks for a change in the air pressure, as detected using the pressure sensor. The start of the air pressure change is registered as the inhale event time 24. The point at which the air pressure change is greatest corresponds to the peak inhalation flow 26. The use determination system 12 records the peak inhalation flow 26 as a flow of air, measured in units of 100 mL per minute, which flow of air is transformed from the air pressure change. Thus, in this example, the at least one value comprises a value of the peak inhalation flow in units of 100 mL per minute. The corresponding usage information provided via the user interface may, for example, express this peak inhalation flow using the same units or in liters per minute.

The time to peak inhalation flow 28 corresponds to the time taken in milliseconds for the peak inhalation flow 26 to be reached. The inhalation duration 30 corresponds to the duration of the entire inhalation in milliseconds. The area under the graph 32 corresponds to the inhalation volume in milliliters.

The usage information provided via the user interface may, additionally or alternatively to providing the inhalation parameter(s) as numerical values, provide a classification of one or more (or each) inhalation event(s). For example, if the peak inhalation flow is between 0 and 30 liters per minute, the inhalation event is classified as "low inhalation" (less than or equal to 30 liters per minute) or as "no inhalation", if no inhalation is detected within 60 seconds of the mouthpiece cover being open. If the peak inhalation flow is greater than 45 and less than or equal to 200 liters per minute, the inhalation event is classified as a "good inhalation". If the peak inhalation flow is greater than 30 and less than or equal to 45 liters per minute, the inhalation event is classified as "fair". If the peak inhalation flow is above 200 liters per minute, the inhalation event is classified as a "possible air vent block". The inhalation event may be classified as an "exhalation", which may be sensed by airflow being detected in the opposite direction to that expected for inhalation using the inhaler 100.

In a non-limiting example, the inhaler is configured such that, for a normal inhalation, the medicament is dispensed approximately 0.5 seconds following the start of the inhalation. A subject's inhalation only reaching peak inhalation flow after the 0.5 seconds have elapsed, such as after approximately 1.5 seconds, may be partially indicative of the subject having difficulty in controlling their respiratory disease. Such a time to reach peak inhalation flow may, for example, be indicative of the subject facing an impending exacerbation.

More generally, the use determination system 12 may employ respective sensors (e.g. respective pressure sensors) for registering an inhalation/use of the inhaler and detecting the inhalation parameter, or a common sensor (e.g. a common pressure sensor) which is configured to fulfil both inhalation/use registering and inhalation parameter detecting functions.

Any suitable sensor may be included in the use determination system 12, such as one or more pressure sensors, temperature sensors, humidity sensors, orientation sensors, acoustic sensors, and/or optical sensors. The pressure sensor(s) may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology.

In a non-limiting example, the use determination system 12 comprises a differential pressure sensor. The differential pressure sensor may, for instance, comprise a dual port type sensor for measuring a pressure difference across a section of the air passage through which the subject inhales. A single port gauge type sensor may alternatively be used. The latter operates by measuring the difference in pressure in the air passage during inhalation and when there is no flow. The difference in the readings corresponds to the pressure drop associated with inhalation.

In another non-limiting example, the use determination system 12 includes an acoustic sensor. The acoustic sensor in this example is configured to sense a noise generated when the subject inhales through the respective inhaler 100. The acoustic sensor may include, for example, a microphone. The respective inhaler 100 may, for instance, comprise a capsule which is arranged to spin when the subject inhales though the device; the spinning of the capsule generating the noise for detection by the acoustic sensor. The spinning of the capsule may thus provide a suitably interpretable noise, e.g. rattle, for deriving use and/or inhalation parameter data.

An algorithm may, for example, be used to interpret the acoustic data in order to determine use data and/or the parameter relating to airflow during the inhalation. For instance, an algorithm as described by P. Colthorpe et al., "Adding Electronics to the Breezhaler: Satisfying the Needs of Patients and Regulators", Respiratory Drug Delivery 2018, 1, 71-80 may be used. Once the generated sound is detected, the algorithm may process the raw acoustic data to generate the use and/or inhalation parameter data.

Figure 3:
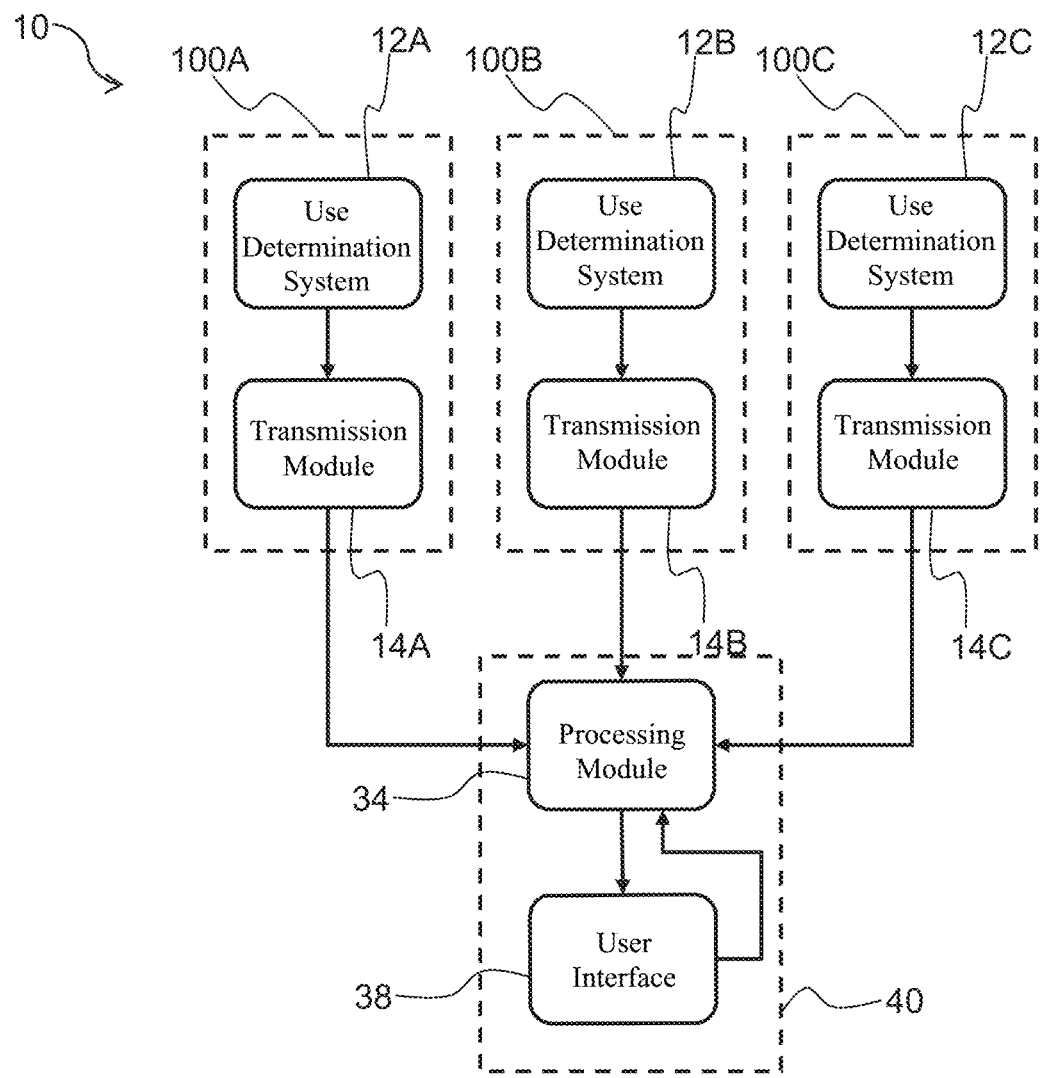
FIG. 3 shows a block diagram of a system according to an example.

FIG. 3 shows a block diagram of a system 10 according to a non-limiting example. The system 10 may, for example, be alternatively termed "an inhaler assembly".

As shown in FIG. 3, the system 10 comprises a first inhaler 100A comprising a first use determination system 12A, and a first transmission module 14A. The system 10 further comprises a second inhaler 100B comprising a second use determination system 12B, and a second transmission module 14B. The first inhaler 100A delivers a first medicament, and the second inhaler 100B delivers a second medicament which is different from the first medicament, as previously described.

Whilst not essential in the context of the present disclosure, the system 10 depicted in FIG. 3 further comprises a third inhaler 100C comprising a third use determination system 12C, and a third transmission module 14C. The third inhaler 100C delivers a third medicament which is different from the first and second medicaments. In other examples, no third inhaler 100C is included in the system 10, or a fourth, fifth, etc. inhaler (not visible) is included in addition to the first inhaler 100A, the second inhaler 100B, and the third inhaler 100C. Alternatively or additionally, the system 10 includes a plurality of first inhalers 100A, a plurality of second inhalers 100B, and so on, as previously described.

The system 10 comprises a processing module 34 which is configured to receive the respective encrypted data transmitted from each of the transmission modules 14A, 14B, 14C, as represented in FIG. 3 by the arrows between each of the blocks corresponding to the transmission modules 14A, 14B, 14C and the block corresponding to the processing module 34. The first, second, and/or third encrypted data may be transmitted wirelessly to the processing module 34, as previously described. The processing module 34 may thus comprise a suitable receiver or transceiver for receiving the encrypted data. The receiver or transceiver of processing module 34 may be configured to implement the same communication protocols as transmission modules 14A, 14B, 14C and may thus include similar communication hardware and software as transmission modules 14A, 14B, 14C as described herein (not shown in FIG. 3).

The processing module 34 may comprise a suitable processor and memory configured to perform the functions described herein for the processing module. For example, the processor may be a general purpose processor programmed with computer executable instructions for implementing the functions of the processing module. The processor may be implemented using a microprocessor or microcontroller configured to perform the functions of the processing module. The processor may be implemented using an embedded processor or digital signal processor configured to perform the functions of the processing module. In an example, the processor may be implemented on a smartphone or other consumer electronic device that is capable of communicating with transmission modules 14A, 14B, 14C and performing the functions of the processing module 34 as described herein. For example, the processing module may be implemented on a smart phone or consumer electronic device that includes an application (e.g., app) that causes the processor of the smartphone or other consumer electronic device to perform the functions of the processing module 34 as described herein.

The processing module 34 distinguishes between the first encrypted data, the second encrypted data, and the third encrypted data, for example by using respective identifiers, as previously described.

The processing module 34 determines first usage information relating to the first medicament based on the distinguished first encrypted data. The first usage information may comprise a registered use of, or inhalation performed using, the first inhaler 100A, and/or a parameter relating to airflow during such an inhalation using the first inhaler 100A, as previously described.

Similarly, the processing module 34 determines second and third usage information relating to the second and third medicaments respectively, based on the distinguished second and third encrypted data.

The system 10 further comprises a user interface 38. The processing module 34 is configured to control the user interface 38 to communicate the first, second, and/or third usage information. The arrow pointing from the block representing the processing module 34 to the block representing the user interface 38 is intended to represent the control signal(s) which causes or cause the user interface to communicate, for example display, the respective usage information. In this respect, the user interface 38 may comprise any suitable display, screen, for example touchscreen, etc. which is capable of displaying the respective usage information. Alternatively or additionally, the respective usage information may be provided by the user interface 38 via an audio message. In such an example, the user interface 38 comprises a suitable loudspeaker for delivering the audio message. Numerous ways of communicating the respective usage information can be used.

The system 10 thus enables the subject to be informed of their usage of the respective medicaments, which may be administered according to a treatment regimen and/or an administration protocol specific to the respective medicament, as previously described.

Whilst the transmission modules 14A, 14B, 14C are each shown in FIG. 3 as transmitting (encrypted) data to the processing module 34, this is not intended to exclude the respective inhalers 100A, 1008, 100C, or a component module thereof, receiving data transmitted from the processing module 34.

In a non-limiting example, a clock module (not visible in the Figures) is included in each of the respective inhalers 100A, 1008, 100C for assigning a time, for example a time stamp, to the usage parameter of the respective inhaler 100A, 1008, 100C. In this example, the processing module 34 is configured to synchronize the clock modules of the respective inhalers 100A, 1008, 100C. Such synchronization may, for instance, provide a point of reference which enables the relative timing of use of the respective inhalers 100A, 1008, 100C to be determined, which may have clinical relevance, as previously described. The assigned time, for example time stamp, may, for instance, be included in the usage information for the respective medicaments communicated, e.g. displayed, by the user interface 38.

Whilst not shown in FIG. 3, the processing module 34 may, in some examples, comprise a further clock module. The clock modules of each of the respective inhalers 100A, 1008, 100C may thus be synchronized according to the time provided by the further clock module. The further clock module may, for instance, receive the time of the time zone in which the processing module 34 is situated. This may cause the respective inhalers 100A, 1008, 100C to be synchronized according to the time in which the subject and their respective inhalers 100A, 1008, 100C are located, which may provide further information of clinical relevance, as previously described.

In an embodiment, the processing module 34 is at least partly included in a first processing module included in the user device 40. By implementing as much processing as possible of the usage data from the respective inhalers 100A, 1008, 100C in the first processing module of the user device 40, battery life in the respective inhalers 100A, 1008, 100C may be advantageously saved. The user device 40 may be, for example, at least one selected from a personal computer, a tablet computer, and a smart phone.

Alternatively or additionally, the user interface 38 may be at least partly defined by a first user interface of the user device 40. The first user interface of the user device 40 may, for instance, comprise, or be defined by, the touchscreen of a smart phone 40.

In other non-limiting examples, the processing module is not included in a user device. The processing module (or at least part of the processing module 34) may, for example, be provided in a server, e.g. a remote server.

FIG. 4 shows front and rear views of the exterior of an inhaler 100 according to a non-limiting example. The inhaler 100 comprises a top cap 102, a main housing 104, a mouthpiece 106, a mouthpiece cover 108, and an air vent 126. The mouthpiece cover 108 may be hinged to the main housing 104 so that it may open and close to expose the mouthpiece 106 and the air vent 126. The depicted inhaler 100 also comprises a mechanical dose counter 111, whose dose count may be used to check the number of doses remaining as determined by the processing module (on the basis of the total number of doses contained by the inhaler 100 prior to use and on the uses determined by the use determination system 12), as previously described.

In the non-limiting example shown in FIG. 4, the inhaler 100 has a barcode 42 printed thereon. The barcode 42 in this example is a quick reference (QR) code printed on the uppermost surface of the top cap 102. The use determination system 12 and/or the transmission module 14 may, for example, be located at least partly within the top cap 102, for example as components of an electronics module (not visible in FIG. 4). The electronics module of the inhaler 100 will be described in greater detail with reference to FIGS. 12 to 15.

The QR code is more clearly visible in FIG. 5, which provides a view from directly above the top cap 102 of the inhaler 100 shown in FIG. 4. The QR code 42 may provide a facile way of pairing the respective inhaler 100 with the processing module 34, in examples in which the user device 40 comprises a suitable optical reader, such as a camera, for reading the QR code. FIG. 6 shows a user pairing the inhaler 100 with the processing module 34 using the camera included in the user device 40, which in this particular example is a smart phone.

Such a bar code 42, e.g. QR code, may comprise the identifier which is assigned to the respective medicament of the inhaler 100, as previously described. Table 1 provides a non-limiting example of the identifiers included in the QR code 42 for various inhalers 100.

TABLE 1

| Identifier in QR code | Brand of inhaler | Medicament | Dose strength (mcg) | Total dose count of inhaler prior to use | Medicament identification number |
|---|---|---|---|---|---|
| <blank> | ProAir Digihaler | albuterol | 117 | 200 | AAA200 |
| AAA030 | ProAir Digihaler | albuterol | 117 | 30 | AAA030 |
| FSL060 | AirDuo Digihaler | fluticasone/ salmeterol | 55/14 | 60 | FSL060 |
| FSM060 | AirDuo Digihaler | fluticasone/ salmeterol | 113/14 | 60 | FSM060 |
| FSH060 | AirDuo Digihaler | fluticasone/ salmeterol | 232/14 | 60 | FSH060 |
| FPL060 | ArmonAir Digihaler | fluticasone | 55 | 60 | FPL060 |
| FPM060 | ArmonAir Digihaler | fluticasone | 113 | 60 | FPM060 |
| FPH060 | ArmonAir Digihaler | fluticasone | 232 | 60 | FPH060 |

As shown in Table 1, the identifier further denotes the dose strength and the total dose count of the inhaler prior to use. The processing module 34 may use the former to, in combination with the usage information, control the user interface 38 to issue a notification when the label recommended dosages have been exceeded, as previously described. Alternatively or additionally, the processing module 34 may use the total dose count of the inhaler prior to use and the usage information to determine the number of doses remaining in the respective inhaler 100, as previously described.

The barcode 42, e.g. QR code, on the inhaler may, for instance, further comprise a security key, for example in the form of a series of alphanumerical characters, for preventing unauthorized users from accessing the respective inhaler 100. The processing module 34 may be able to decrypt the respective encrypted data once the processing module 34 has been provided with the security key, but may not be able to decrypt the respective encrypted data before the processing module 34 has been provided with the security key. More generally, the security key may be included in the respective identifier.

In a non-limiting example, the system is configured to restrict one or more, e.g. each, of the inhalers included in the system to a single user account.

In such an example, a passkey, e.g. provided in the QR code, may allow synchronization between the respective inhaler and the processing module of the system. The passkey and, in turn, the usage parameter data, e.g. inhalation and/or usage data, from the respective inhaler may be public. This public inhalation data may not be associated with the particular subject until synchronization with the single user account.

Since the system is configured to restrict the respective inhaler to being associated with the single user account, the respective inhaler may be prevented from being synchronized with another user account, for example in situations where the inhaler is lost or stolen. In this way, third parties may be prevented from acquiring usage parameter data which is not theirs.

In other non-limiting examples, the processing module 34 may be paired with the respective inhaler 100 by, for example, manual entry of an alphanumerical key including the respective identifier via the user interface, e.g. a touchscreen.

Figure 7:
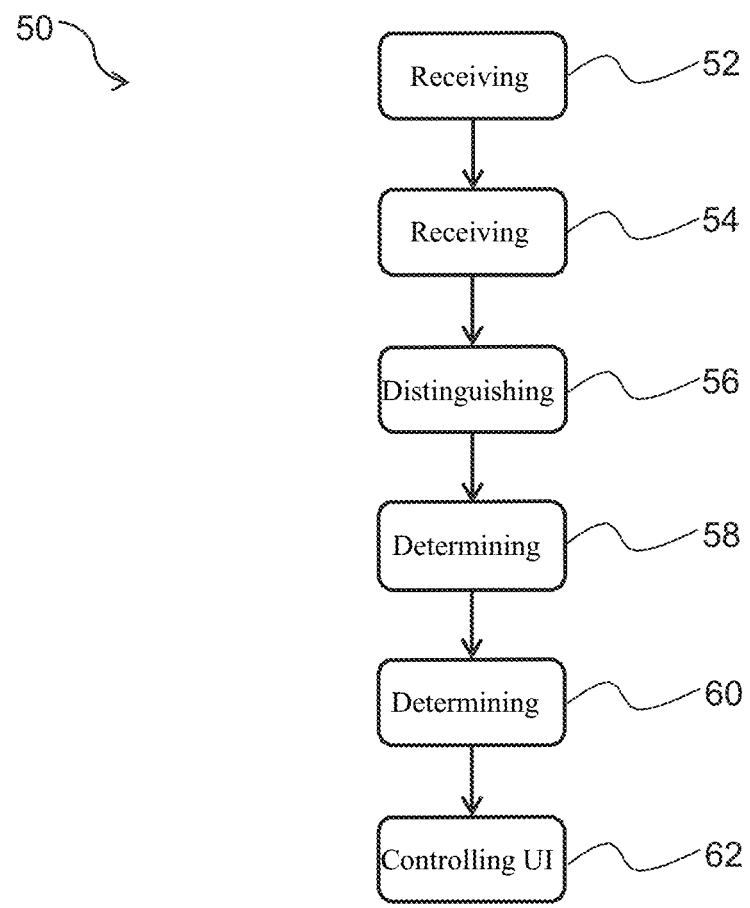
FIG. 7 provides a flowchart of a method according to an example.

FIG. 7 provides a flowchart of a method 50 according to an example. The method 50 comprises receiving 52 first encrypted data from a first transmission module of a first inhaler configured to deliver a first medicament to a subject. The first encrypted data is based on a first value of a usage parameter relating to use of the first inhaler determined by a first use determination system included in the first inhaler, as previously described.

Second encrypted data is received 54 from a second transmission module included in a second inhaler configured to deliver a second medicament to the subject. The second encrypted data is based on a second value of a usage parameter relating to use of the second inhaler. The second medicament is different from the first medicament;

The method further comprises distinguishing 56 between the first encrypted data and the second encrypted data, and determining 58 first usage information relating to the first medicament from the distinguished first encrypted data. Second usage information relating to the second medicament is determined 60 from the distinguished second encrypted data. A user interface is controlled 62 to display the first and second usage information. As one non-limiting examples, the user interface may display a GUI that displays the first and second usage information, for example, simultaneously in a single GUI.

In an embodiment, the receiving 52 the first encrypted data comprises receiving the first encrypted data from each respective first transmission module of a plurality of first inhalers, each of said plurality of first inhalers being configured to deliver the first medicament.

Alternatively or additionally, the receiving 54 the second encrypted data may comprise receiving the second encrypted data from each respective second transmission module of a plurality of second inhalers, each of said plurality of second inhalers being configured to deliver the second medicament.

Whilst not shown in FIG. 7, the method 50 may further comprise receiving third encrypted data from a third transmission module included in a third inhaler configured to deliver a third medicament which is different from the first and second medicaments. In such an example, the method 50 comprises distinguishing the third encrypted data from the first encrypted data and the second encrypted data, and determining third usage information relating to the third medicament from the distinguished third encrypted data. The user interface is controlled to display the third usage information.

The method 50 may comprise receiving identifiers, each identifier being assigned according to the medicament which is delivered by the respective inhaler. The respective identifiers may then be used to distinguish 56 the respective encrypted data, as previously described.

A clock module may, for instance, be included in each of the respective inhalers for assigning a time to said usage parameter of the respective inhaler. In such an example, the method 50 further comprises synchronizing the clock modules of the respective inhalers. The time assigned to the usage parameter may, for example, be included in the usage information for the respective medicaments. The synchronizing may in some examples comprise synchronizing each of the respective clock modules with the time of the time zone in which the respective inhalers are situated, as previously described.

In a non-limiting example, the processing module determines a use and/or system error based on the encrypted data received from one or more, e.g. each, of the inhalers included in the system. Such a use error may, for example, be indicative of potential misuse of the respective inhaler or inhalers. The system error may be indicative of a fault with a component of the respective inhaler, such as the use determination system and/or the transmission module of the respective inhaler. A system error may, for example, include a hardware fault of the respective inhaler. The user interface may be controlled by the processing module to provide an alert or notification based on the determined use and/or system error (e.g., such as providing an alert or notification for the determined use and/or system errors of each of a plurality of different inhalers, potentially including different medicaments).

A use error may, for example, include a low inhalation event, a no inhalation event, and/or an excessive inhalation event. Such events will be described in more detail below with reference to FIG. 16.

A use error may alternatively or additionally include one or more of: the mouthpiece cover being left open for more than a predetermined time period, e.g. 60 seconds; multiple inhalations being recorded in respect of a single actuation of the above-described mechanical switch, for example a second inhalation performed within the same mouthpiece cover open/closed session; and an exhalation through the flow pathway, as determined from a positive pressure change being sensed in the flow pathway.

When the use error relates to the mouthpiece cover being left open for more than the predetermined time period, the inhalers detection circuitry may only stay active for the predetermined time period to preserve battery life. This may mean that anything which would otherwise be detectable/determinable by the use determination system that occurs outside of this predetermined time period is not detected/recorded. Notifying the user of this error may therefore serve the purpose of informing the user that otherwise detectable events are not detected outside the predetermined time period triggered by opening of the mouthpiece cover.

It is noted that the abovementioned exhalation-based use error may not be recorded if such an exhalation is sensed subsequently to an inhalation being performed in respect of a given actuation of the mechanical switch, e.g. within the same mouthpiece cover open/closed session.

System errors may include one or more of: a problem occurring when saving inhalation data to a memory included in the inhaler, such as a memory included in the use determination system ("corrupted data error"); an error with the clock module of the inhaler ("time stamp error"); and an error relating to collecting information about the inhalation ("inhalation parameter error").

In a particular example, use and/or system errors from more than one, e.g. all of, the inhalers included in the system are collected, e.g. aggregated, by the processing module. The processing module is further configured to control the user interface to provide the alert or notification based on the collected use and/or system errors. For instance, the processing module controls the user interface to provide the alert or notification based on the number of use and/or system errors collected from the inhalers included in the system reaching or exceeding a predetermined number of use and/or system errors.

Figure 8:
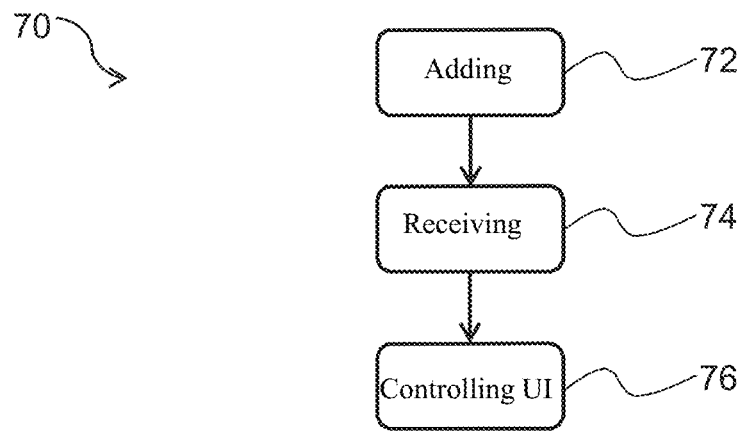
FIG. 8 provides a flowchart of a method according to another example.

As shown in FIG. 8, the present disclosure further provides a method 70 comprising adding 72 a further inhaler configured to dispense a medicament to a system comprising a processing module, a user interface, and an existing inhaler which is also configured to dispense the medicament. The further inhaler includes a (further) use determination system and a (further) transmission module, and the existing inhaler includes an existing use determination system and an existing transmission module. Such use determination systems and transmission modules have already been described above, so a further description here will be omitted for the sake of brevity only.

The method 70 comprises receiving 74 an identifier provided with the further inhaler, for example via a barcode, such as a QR code, printed on the further inhaler or its packaging, as previously described. The identifier denotes at least the medicament and the dose strength of the medicament. The method further comprises using 76 the processing module to control the user interface to issue at least one notification if the dose strength of the medicament in the further inhaler as denoted by the identifier is different from the dose strength of the medicament in the existing inhaler.

The at least one notification may, for example, comprise a notification informing the subject that the dose strength of the further inhaler is different from that of the existing inhaler and/or a notification to request that the subject discards the existing inhaler. In this manner, the system may assist the subject to adjust to a prescription change.

The present disclosure further provides a method comprising determining whether a medicament of a further inhaler which is added to a system, which system comprises a processing module, a user interface, and an existing inhaler which delivers a maintenance medicament, is a further maintenance medicament.

The further inhaler includes a (further) use determination system and a (further) transmission module, and the existing inhaler includes an existing use determination system and an existing transmission module. Such use determination systems and transmission modules have already been described above, so a further description here will be omitted for the sake of brevity only.

The determination of whether the medicament is a further maintenance medicament may, for example, be based on an identifier which identifies that the further medicament is a maintenance medicament or is a different medicament type, such as a rescue medicament. The identifier may be received by the processing module of the system, and the processing module may implement the determination. Such an identifier may, for example, be included in a QR code of the further inhaler, as previously described.

If the medicament is identified as a further maintenance medicament, the method may further comprise controlling the user interface to prompt the user to select one of the existing inhaler and the further inhaler. Reminders may then be issued, e.g. by the processing module controlling the user interface to provide such reminders, according to the user selection to remind the subject to use the existing inhaler or the further inhaler according to a treatment regimen relating to administering of the maintenance medicament or the further maintenance medicament respectively.

In this manner, the method (or the system which is configured to implement the method) may limit such reminders to one maintenance inhaler. In other words, for instances where the subject is prescribed multiple maintenance inhalers, the user selection may cause the system to provide reminders for the selected maintenance inhaler, but not provide reminders for the maintenance inhaler which was not selected. The subject or user may select the particular maintenance inhaler based on the specific or current treatment regimen of the subject.

Alternatively or additionally, the method may comprise, based on the determination that the medicament is a further maintenance medicament, providing an alert, e.g. via the user interface and/or by transmitting a notification to a healthcare provider, that the system comprises both the maintenance medicament and the further maintenance medicament.

Such an alert may, for example, comprise a message informing the user or subject to verify with their healthcare provider (and/or doctor) that a plurality of maintenance medicaments are prescribed for the subject.

Such an example may be applicable when, for instance, the subject is prescribed two maintenance medicaments at the same time, e.g. when the subject is transitioning between maintenance treatments. When the further inhaler is added to the system, for example when the QR code of the further inhaler is scanned, the processing module may be configured to provide the alert, e.g. by controlling the user interface and/or by transmitting the alert to the subject's healthcare provider.

Also provided is a computer program comprising computer program code which is adapted, when the computer program is run on a computer, to implement any of the above-described methods. In a preferred embodiment, the computer program takes the form of an app, for example an app for a user device 40, such as a mobile device, e.g. tablet computer or a smart phone.

Figure 9:
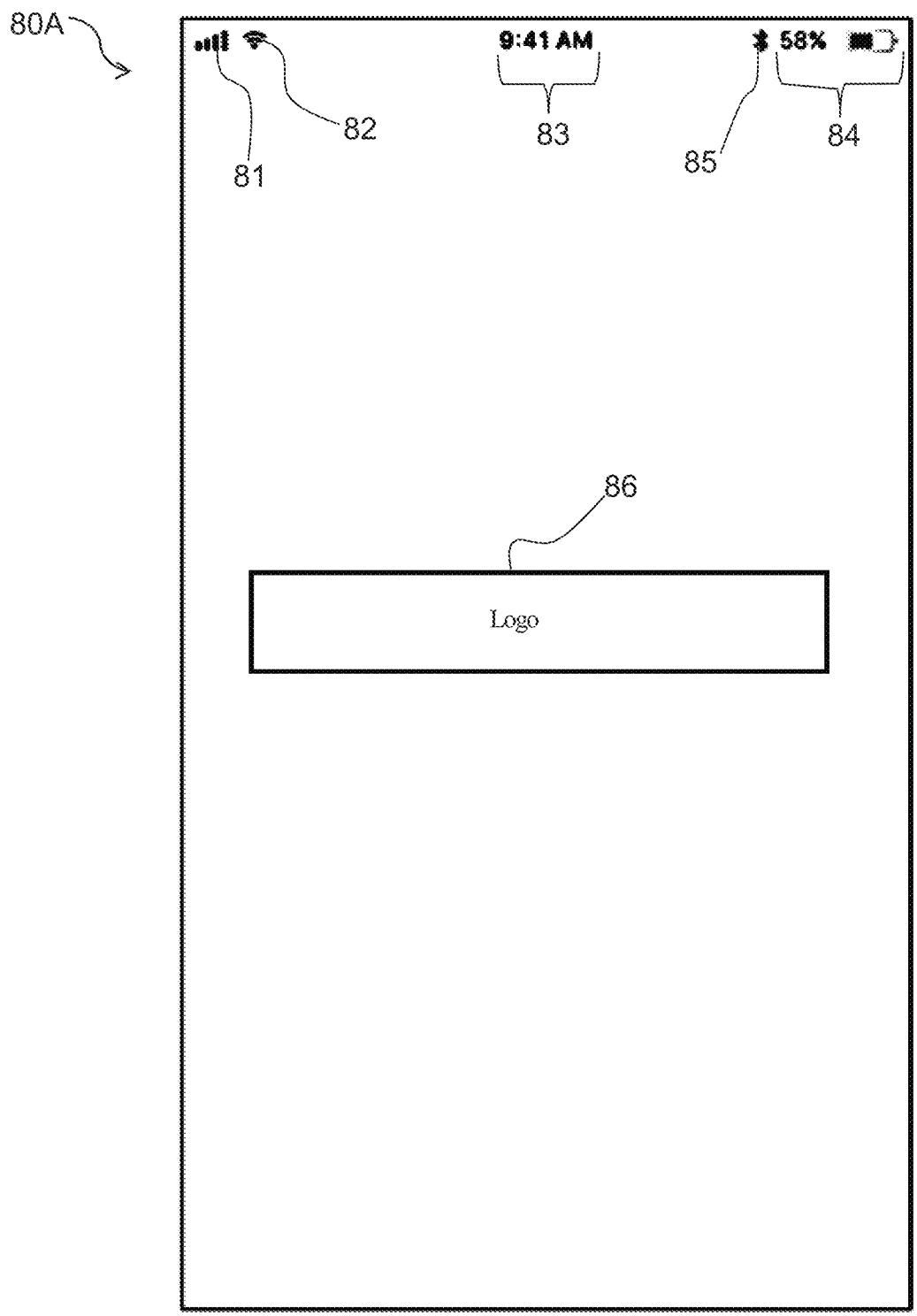
FIG. 9 provides a first view of a user interface according to an example.

FIG. 9 provides a first view of a user interface 38 according to a non-limiting example. In this example, the user interface 38 comprises the screen of a smart phone, which smart phone defines the user device 40. Symbol 81 denotes the signal strength of the cellular signal being received by the smart phone 40.

Symbol 82 denotes that the smart phone 40 is connected to WiFi. The time 83 provided by the (further) clock module included in the processing module 34 of the smart phone 40. This time 83 may be used to synchronize the respective clock modules of the inhalers 100A, 100B included in the system 10, as previously described.

The battery life 84 of the user device 40 is also displayed by the user interface 38. Symbol 85 indicates that Bluetooth® is enabled. At least one of the cellular signal 81, WiFi 82, and Bluetooth® 84 may be used to communicate with the respective inhaler 100A, 100B. Bluetooth® may be preferred, as previously explained.

The screenshot view 80A provided in FIG. 9 may be regarded as a "splash screen" which is presented while the app is being launched. Box 86 denotes the position of a logo relating to the respective inhaler 100A, 100B and/or app provider.

Figure 10:
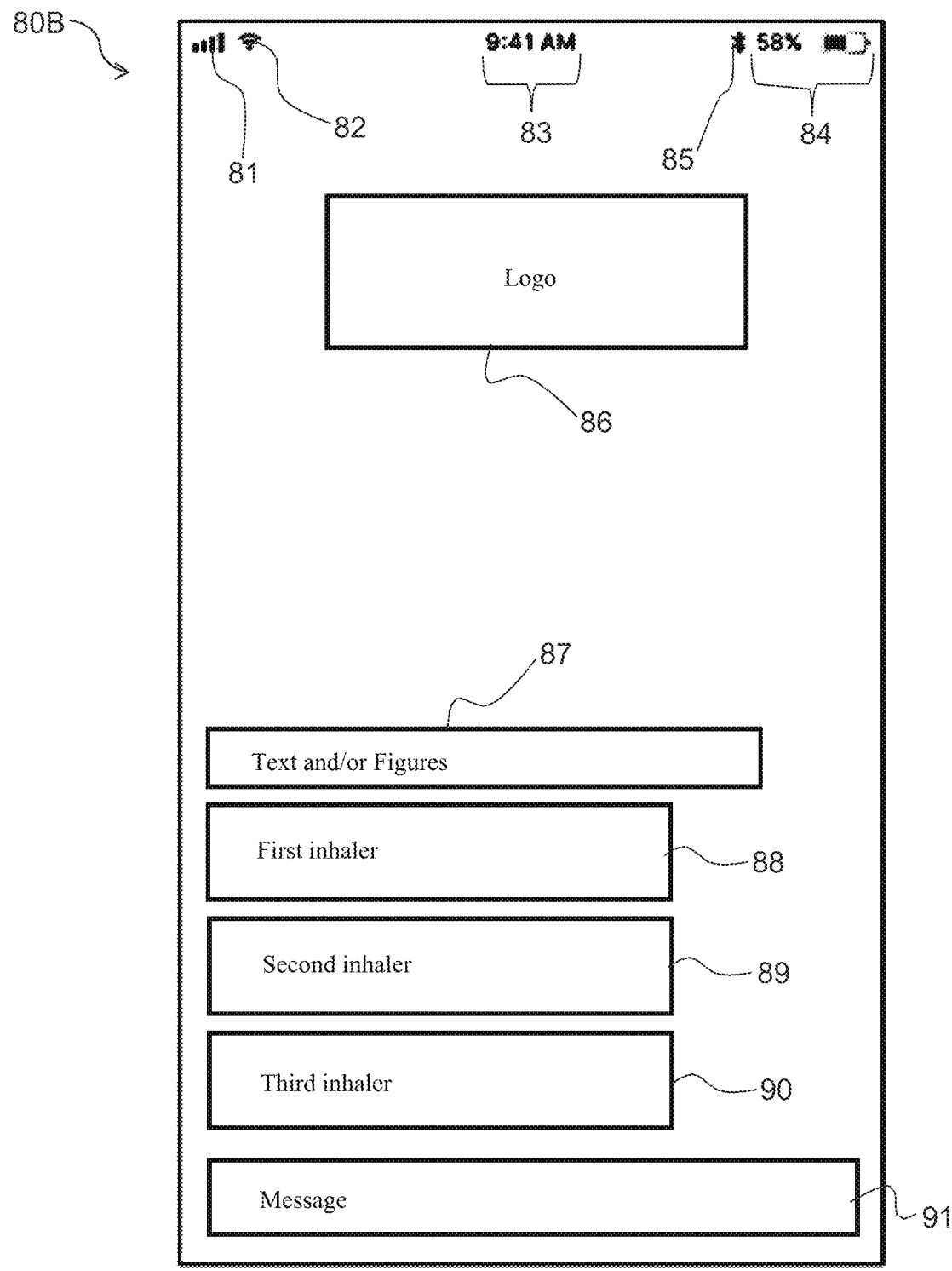
FIG. 10 provides a second view of a user interface according to an example.

FIG. 10 provides a second view 80B of the user interface 38. In this screenshot view 80B, the logo 86 is accompanied by details of the inhalers 100A, 100B, 100C supported by the app. Box 87 includes text and/or figures communicating that the app supports the inhalers 100A, 100B, 100C. Box 88 denotes the first inhaler 100A, box 89 denotes the second inhaler 100B, and box 90 denotes the third inhaler 100C, although the provision of more than two inhalers 100 is non-essential in the context of the present disclosure.

Box 91 provides a message for the subject to study safety information and full prescribing information in a relevant section of the app.

Figure 11:
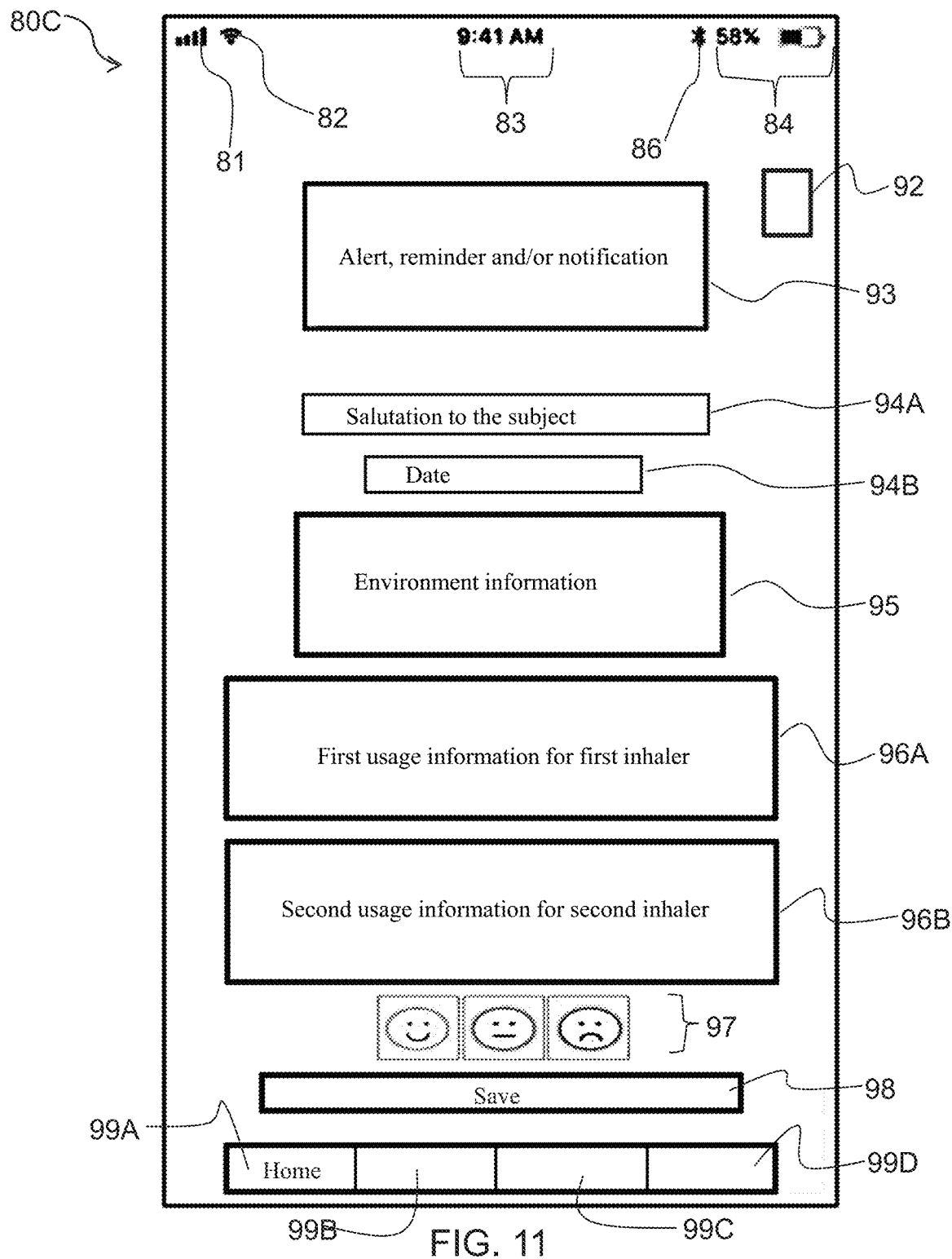
FIG. 11 provides a third view of a user interface according to an example.

FIG. 11 provides a third view of the user interface 38. This screenshot view 80C provides touch points and information relating to usage of the respective inhalers 100A, 100B, 100C. Box 91 is a touchpoint which enables the subject to view the connectivity status, e.g. Bluetooth® connectivity status, of the respective inhalers 100A, 100B, 100C.

Box 93 may provide an alert, reminder and/or notification. For instance, box 93 may contain a text or pictorial reminder for the subject to administer a maintenance medicament.

Box 94A may provide a salutation to the subject, for example using the time of the day associated with the time 83. Box 94B provides the date.

Box 95 provides environment information at the subject's location, such as weather, temperature, and/or humidity information. Such information may have relevance to the subject's management of their respiratory disease. The processing module 34 may be configured to retrieve such environment information, for example from a suitable third party internet source, and control the user interface 34 to display the retrieved environment information.

Box 96A provides first usage information relating to use of the first inhaler 100A. For example, the subject may be informed of registered uses of the first inhaler 100A during the day thus far, during the past 7 days, during the past 30 days, and so on. The box 96A may also provide a reminder to the subject to administer the first medicament at a certain point in the future.

Similarly, box 96B provides second usage information relating to use of the second inhaler 100B. The subject may, for example, be informed of registered uses of the second inhaler 100B during the day thus far, during the past 7 days, during the past 30 days, and so on.

The icons 97 in FIG. 11 enable the subject to input a self-assessment, for example a daily self-assessment, relating to how the subject is feeling, particularly in relation to the symptoms of the subject's respiratory disease. In this non-limiting example, the subject selects one of three emoji-type icons according to how they are feeling that day. Box 98 is a touchpoint which is pressed by the subject to save their daily self-assessment.

The view 80C shown in FIG. 11 may be a home screen 99A, but tabs 99B, 99C, and 99D enable other screens to be accessed. Tab 99B enables the subject to access a data screen which provides further usage information from the respective inhalers 100A, 100B, 100C. Tab 99C enables the subject to access a screen summarizing the inhalers 100A, 100B, 100C connected to the processing module 34. Tab 80C enables the subject to view their profile, which may contain personal data concerning the subject, such as name, date of birth, and so on.

FIGS. 12-15 provide a non-limiting example of an inhaler arrangement 100 which may be included in the system 10.

Figure 12:
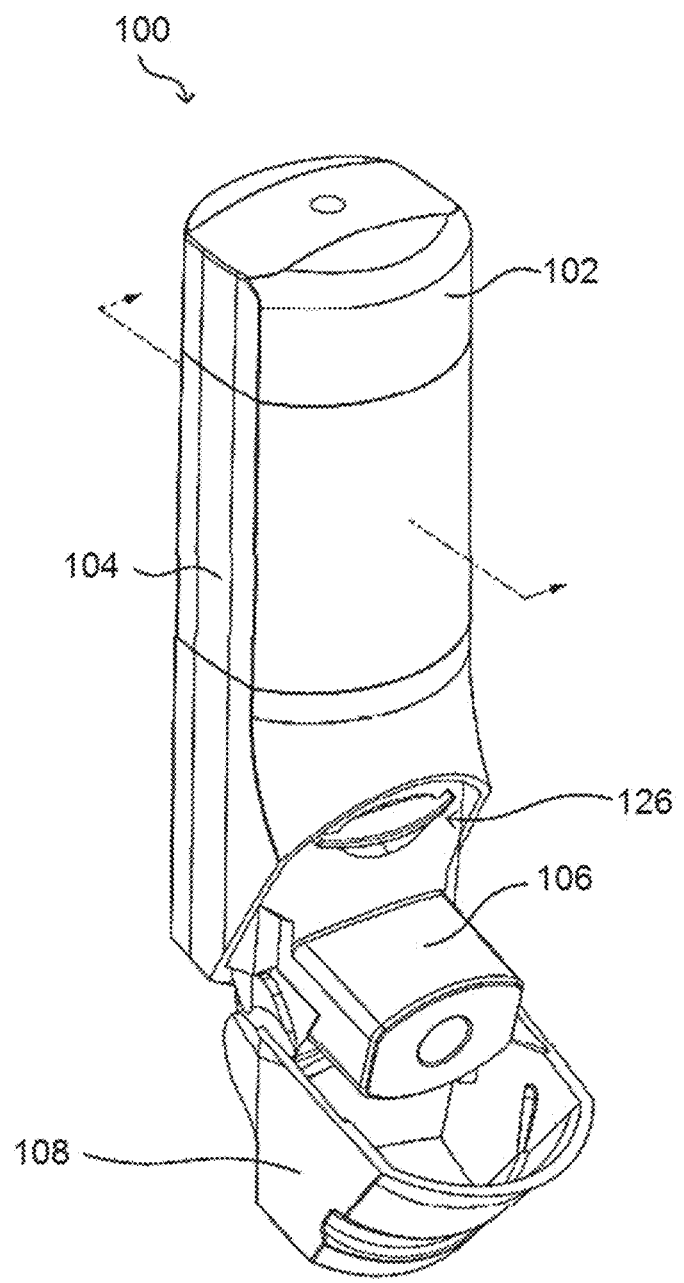
FIG. 12 shows a front perspective view of an exemplary inhaler.

FIG. 12 provides a front perspective view of an inhaler arrangement 100, referred to as "an inhaler" from here on, according to a non-limiting example. The inhaler 100 may, for example, be a breath-actuated inhaler. The inhaler 100 may include a top cap 102, a main housing 104, a mouthpiece 106, a mouthpiece cover 108, an electronics module 120, and an air vent 126. The mouthpiece cover 108 may be hinged to the main housing 104 so that it may open and close to expose the mouthpiece 106.

Although illustrated as a hinged connection, the mouthpiece cover 106 may be connected to the inhaler 100 through other types of connections. Moreover, while the electronics module 120 is illustrated as housed within the top cap 102 at the top of the main housing 104, the electronics module 120 may be integrated and/or housed within the main body 104 of the inhaler 100.

The electronics module 120 may, for instance, include the above-described use determination system 12 and the transmission module 14. For example, the electronics module 120 may include a processor, memory configured to perform the functions of use determination system 12 and/or transmission module 14. The electronics module 120 may include switch(es), sensor(s), slider(s), and/or other instruments or measurement devices configured to determine inhaler usage information as described herein. The electronics module 120 may include a transceiver and/or other communication chips or circuits configured to perform the transmission functions of transmission module 14.

Figure 13:
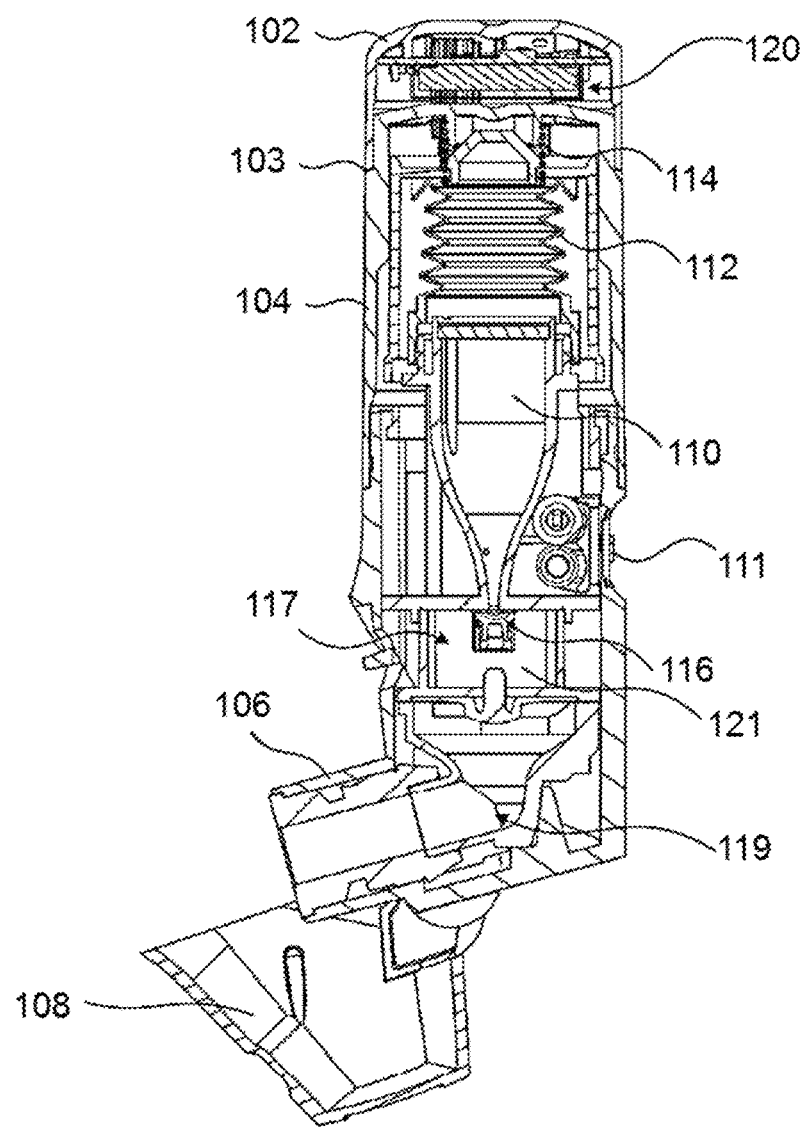
FIG. 13 shows a cross-sectional interior perspective view of the inhaler shown in FIG. 12.

FIG. 13 provides a cross-sectional interior perspective view of the example inhaler 100. Inside the main housing 104, the inhalation device 100 may include a medication reservoir 110 and a dose metering assembly. For example, the inhaler 100 may include a medication reservoir 110 (e.g. a hopper), a bellows 112, a bellows spring 114, a yoke (not visible), a dosing cup 116, a dosing chamber 117, a deagglomerator 121, and a flow pathway 119. The medication reservoir 110 may include medication, such as dry powder medication, for delivery to the subject. Although illustrated as a combination of the bellows 112, the bellows spring 114, the yoke, the dosing cup 116, the dosing chamber 117, and the deagglomerator 121, the dose metering assembly may include a subset of the components described and/or the inhalation device 100 may include a different dose metering assembly (e.g., based on the type of inhalation device, the type of medication, etc.). For instance, in some examples the medication may be included in a blister strip and the dose metering assembly, which may include one or more wheels, levers, and/or actuators, is configured to advance the blister strip, open a new blister that includes a dose of medication, and make that dose of medication available to a dosing chamber and/or mouthpiece for inhalation by the user.

When the mouthpiece cover 108 is moved from the closed to the open position, the dose metering assembly of the inhaler 100 may prime a dose of medicament. In the illustrated example of FIG. 13, the mouthpiece cover 108 being moved from the closed to the open position may cause the bellows 112 to compress to deliver a dose of medication from the medication reservoir 110 to the dosing cup 116. Thereafter, a subject may inhale through the mouthpiece 106 in an effort to receive the dose of medication.

The airflow generated from the subject's inhalation may cause the deagglomerator 121 to aerosolize the dose of medication by breaking down the agglomerates of the medicament in the dose cup 116. The deagglomerator 121 may be configured to aerosolize the medication when the airflow through the flow pathway 119 meets or exceeds a particular rate, or is within a specific range. When aerosolized, the dose of medication may travel from the dosing cup 116, into the dosing chamber 117, through the flow pathway 119, and out of the mouthpiece 106 to the subject. If the airflow through the flow pathway 119 does not meet or exceed a particular rate, or is not within a specific range, the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, a single dose of medication may remain in the dosing cup until the dose has been aerosolized by the deagglomerator 121. When a dose of medication is delivered, a dose confirmation may be stored in memory at the inhaler 100 as dose confirmation information.

As the subject inhales through the mouthpiece 106, air may enter the air vent to provide a flow of air for delivery of the medication to the subject. The flow pathway 119 may extend from the dosing chamber 117 to the end of the mouthpiece 106, and include the dosing chamber 117 and the internal portions of the mouthpiece 106. The dosing cup 116 may reside within or adjacent to the dosing chamber 117. Further, the inhaler 100 may include a dose counter 111 that is configured to be initially set to a number of total doses of medication within the medication reservoir 110 and to decrease by one each time the mouthpiece cover 108 is moved from the closed position to the open position.

The top cap 102 may be attached to the main housing 104. For example, the top cap 102 may be attached to the main housing 104 through the use of one or more clips that engage recesses on the main housing 104. The top cap 102 may overlap a portion of the main housing 104 when connected, for example, such that a substantially pneumatic seal exists between the top cap 102 and the main housing 104.

Figure 14:
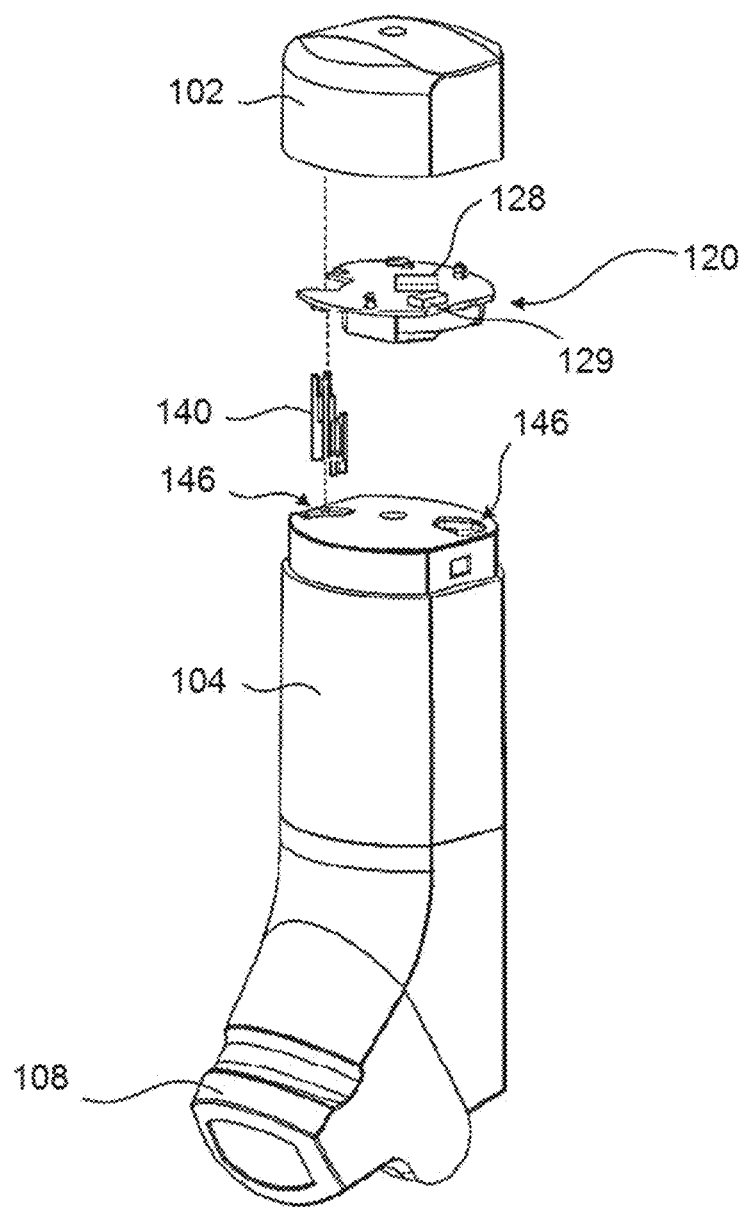
FIG. 14 provides an exploded perspective view of the example inhaler shown in FIG. 12.

FIG. 14 is an exploded perspective view of the example inhaler 100 with the top cap 102 removed to expose the electronics module 120. As shown in FIG. 20, the top surface of the main housing 104 may include one or more (e.g. two) orifices 146. One of the orifices 146 may be configured to accept a slider 140. For example, when the top cap 102 is attached to the main housing 104, the slider 140 may protrude through the top surface of the main housing 104 via one of the orifices 146.

Figure 15:
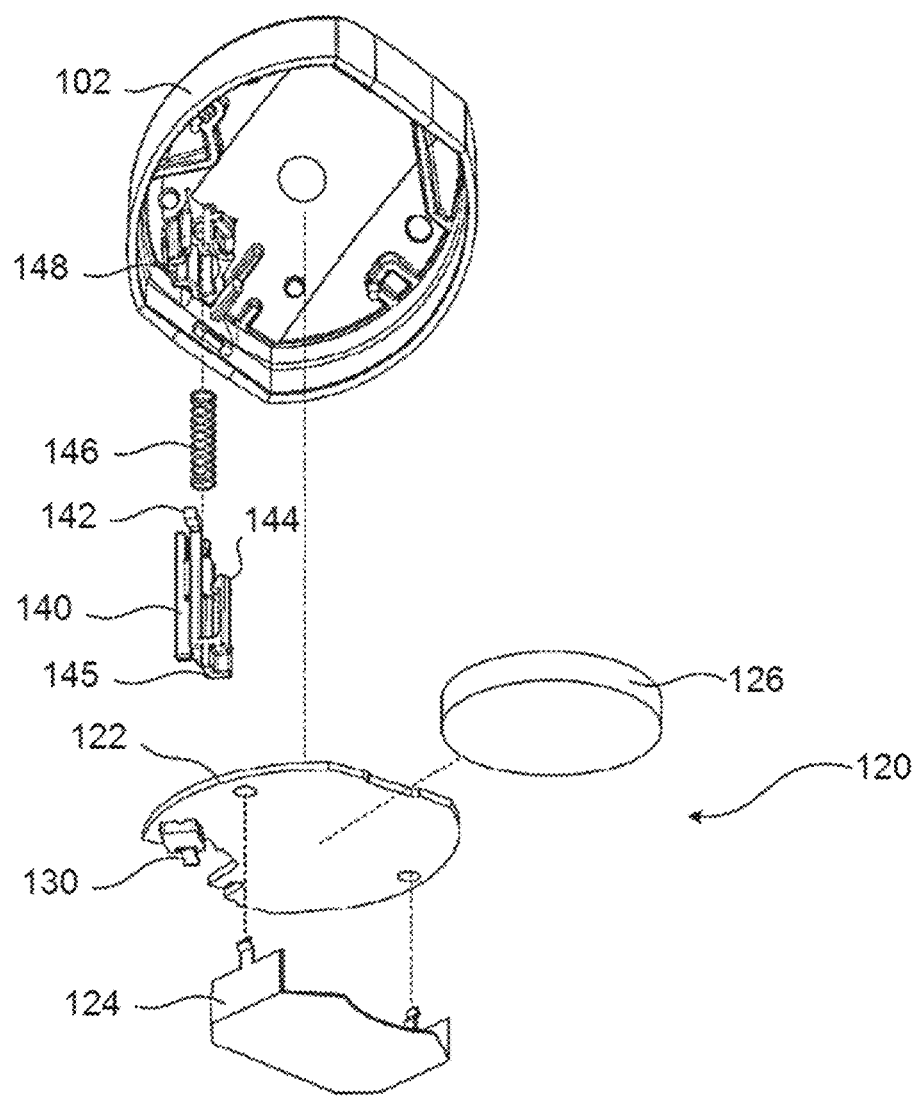
FIG. 15 provides an exploded perspective view of a top cap and electronics module of the inhaler shown in FIG. 12.

FIG. 15 is an exploded perspective view of the top cap 102 and the electronics module 120 of the example inhaler 100. As shown in FIG. 21, the slider 140 may define an arm 142, a stopper 144, and a distal end 145. The distal end 145 may be a bottom portion of the slider 140. The distal end 145 of the slider 140 may be configured to abut the yoke that resides within the main housing 104 (e.g. when the mouthpiece cover 108 is in the closed or partially open position). The distal end 145 may be configured to abut a top surface of the yoke when the yoke is in any radial orientation. For example, the top surface of the yoke may include a plurality of apertures (not shown), and the distal end 145 of the slider 140 may be configured to abut the top surface of the yoke, for example, whether or not one of the apertures is in alignment with the slider 140.

The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g. abut) an upper portion (e.g. a proximate end) of the slider 140. When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke when the mouthpiece cover 108 is closed.

The distal end 145 of the slider 145 may also remain in contact with the yoke while the mouthpiece cover 108 is being opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g. axial) travel of the slider 140. This limit may be less than the vertical travel of the yoke. Thus, as the mouthpiece cover 108 is moved to a fully open position, the yoke may continue to move in a vertical direction towards the mouthpiece 106 but the stopper 144 may stop the vertical travel of the slider 140 such that the distal end 145 of the slider 140 may no longer be in contact with the yoke.

More generally, the yoke may be mechanically connected to the mouthpiece cover 108 and configured to move to compress the bellows spring 114 as the mouthpiece cover 108 is opened from the closed position and then release the compressed bellows spring 114 when the mouthpiece cover reaches the fully open position, thereby causing the bellows 112 to deliver the dose from the medication reservoir 110 to the dosing cup 116. The yoke may be in contact with the slider 140 when the mouthpiece cover 108 is in the closed position. The slider 140 may be arranged to be moved by the yoke as the mouthpiece cover 108 is opened from the closed position and separated from the yoke when the mouthpiece cover 108 reaches the fully open position. This arrangement may be regarded as a non-limiting example of the previously described dose metering assembly, since opening the mouthpiece cover 108 causes the metering of the dose of the medicament.

The movement of the slider 140 during the dose metering may cause the slider 140 to engage and actuate a switch 130. The switch 130 may trigger the electronics module 120 to register the dose metering. The slider 140 and switch 130 together with the electronics module 120 may thus be regarded as being included in the use determination system 12 described above. The slider 140 may be regarded in this example as the means by which the use determination system 12 is configured to register the metering of the dose by the dose metering assembly, each metering being thereby indicative of the inhalation performed by the subject using the inhaler 100.

Actuation of the switch 130 by the slider 140 may also, for example, cause the electronics module 120 to transition from the first power state to a second power state, and to sense an inhalation by the subject from the mouthpiece 106.

The electronics module 120 may include a printed circuit board (PCB) assembly 122, a switch 130, a power supply (e.g. a battery 126), and/or a battery holder 124. The PCB assembly 122 may include surface mounted components, such as a sensor system 128, a wireless communication circuit 129, the switch 130, and or one or more indicators (not shown), such as one or more light emitting diodes (LEDs). The electronics module 120 may include a controller (e.g. a processor) and/or memory. The controller and/or memory may be physically distinct components of the PCB 122. Alternatively, the controller and memory may be part of another chipset mounted on the PCB 122, for example, the wireless communication circuit 129 may include the controller and/or memory for the electronics module 120.

The controller of the electronics module 120 may include a microcontroller, a programmable logic device (PLD), a microprocessor, an application specific integrated circuit (ASIC), a field programmable gate array (FPGA), or any suitable processing device or control circuit.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smart phone.

The sensor system 128 may include one or more sensors. The sensor system 128 may be, for example, included in the use determination system 12 described above. The sensor system 128 may include one or more sensors, for example, of different types, such as, but not limited to one or more pressure sensors, temperature sensors, humidity sensors, orientation sensors, acoustic sensors, and/or optical sensors. The one or more pressure sensors may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology. The sensor system 128 may be configured to provide an instantaneous reading (e.g. pressure reading) to the controller of the electronics module 120 and/or aggregated readings (e.g. pressure readings) over time. As illustrated in FIGS. 13 and 14, the sensor system 128 may reside outside the flow pathway 119 of the inhaler 100, but may be pneumatically coupled to the flow pathway 119.

The controller of the electronics module 120 may receive signals corresponding to measurements from the sensor system 128. The controller may calculate or determine one or more airflow metrics using the signals received from the sensor system 128. The airflow metrics may be indicative of a profile of airflow through the flow pathway 119 of the inhaler 100. For example, if the sensor system 128 records a change in pressure of 0.3 kilopascals (kPa), the electronics module 120 may determine that the change corresponds to an airflow rate of approximately 45 liters per minute (Lpm) through the flow pathway 119.

Figure 16:
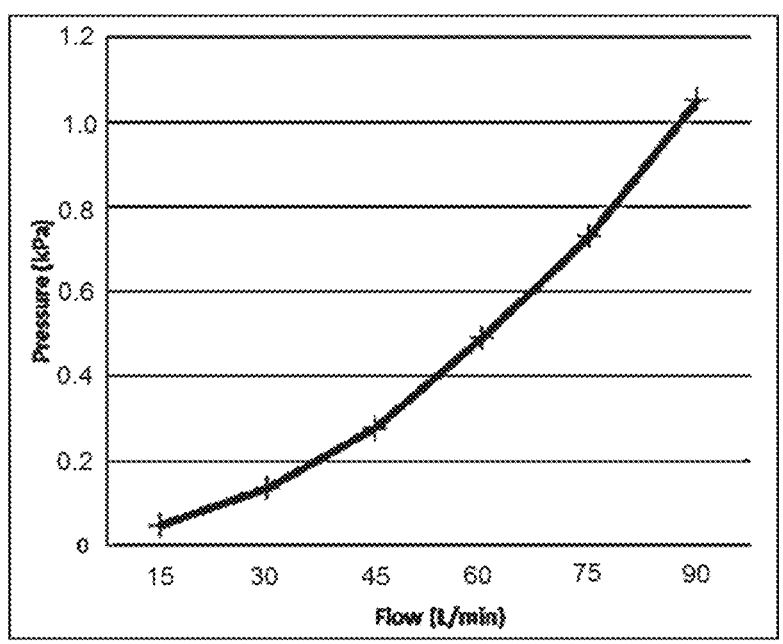
FIG. 16 shows a graph of airflow rate through the example inhaler shown in FIG. 12 versus pressure.

FIG. 16 shows a graph of airflow rates versus pressure. The airflow rates and profile shown in FIG. 16 are merely examples and the determined rates may depend on the size, shape, and design of the inhalation device 100 and its components.

The processing module 34 may generate personalized data in real-time by comparing signals received from the sensor system 128 and/or the determined airflow metrics to one or more thresholds or ranges, for example, as part of an assessment of how the inhaler 100 is being used and/or whether the use is likely to result in the delivery of a full dose of medication. For example, where the determined airflow metric corresponds to an inhalation with an airflow rate below a particular threshold, the processing module 34 may determine that there has been no inhalation or an insufficient inhalation from the mouthpiece 106 of the inhaler 100. If the determined airflow metric corresponds to an inhalation with an airflow rate above a particular threshold, the electronics module 120 may determine that there has been an excessive inhalation from the mouthpiece 106. If the determined airflow metric corresponds to an inhalation with an airflow rate within a particular range, the electronics module 120 may determine that the inhalation is "good", or likely to result in a full dose of medication being delivered.

The pressure measurement readings and/or the computed airflow metrics may be indicative of the quality or strength of inhalation from the inhaler 100. For example, when compared to a particular threshold or range of values, the readings and/or metrics may be used to categorize the inhalation as a certain type of event, such as a good inhalation event, a low inhalation event, a no inhalation event, or an excessive inhalation event. The categorization of the inhalation may be usage parameters stored as personalized data of the subject.

The no inhalation event may be associated with pressure measurement readings and/or airflow metrics below a particular threshold, such as an airflow rate less than or equal to 30 Lpm. The no inhalation event may occur when a subject does not inhale from the mouthpiece 106 after opening the mouthpiece cover 108 and during the measurement cycle. The no inhalation event may also occur when the subject's inspiratory effort is insufficient to ensure proper delivery of the medication via the flow pathway 119, such as when the inspiratory effort generates insufficient airflow to activate the deagglomerator 121 and, thus, aerosolize the medication in the dosing cup 116.

The low inhalation event may be associated with pressure measurement readings and/or airflow metrics within a particular range, such as an airflow rate greater than 30 Lpm and less than or equal to 45 Lpm.

The low inhalation event may occur when the subject inhales from the mouthpiece 106 after opening the mouthpiece cover 108 and the subject's inspiratory effort causes at least a partial dose of the medication to be delivered via the flow pathway 119. That is, the inhalation may be sufficient to activate the deagglomerator 121 such that at least a portion of the medication is aerosolized from the dosing cup 116.

The good inhalation event may be associated with pressure measurement readings and/or airflow metrics above the low inhalation event, such as an airflow rate which is greater than 45 Lpm and less than or equal to 200 Lpm. The good inhalation event may occur when the subject inhales from the mouthpiece 106 after opening the mouthpiece cover 108 and the subject's inspiratory effort is sufficient to ensure proper delivery of the medication via the flow pathway 119, such as when the inspiratory effort generates sufficient airflow to activate the deagglomerator 121 and aerosolize a full dose of medication in the dosing cup 116.

The excessive inhalation event may be associated with pressure measurement readings and/or airflow metrics above the good inhalation event, such as an airflow rate above 200 Lpm. The excessive inhalation event may occur when the subject's inspiratory effort exceeds the normal operational parameters of the inhaler 100. The excessive inhalation event may also occur if the device 100 is not properly positioned or held during use, even if the subject's inspiratory effort is within a normal range. For example, the computed airflow rate may exceed 200 Lpm if the air vent is blocked or obstructed (e.g. by a finger or thumb) while the subject is inhaling from the mouthpiece 106.

Any suitable thresholds or ranges may be used to categorize a particular event. Some or all of the events may be used. For example, the no inhalation event may be associated with an airflow rate which is less than or equal to 45 Lpm and the good inhalation event may be associated with an airflow rate which is greater than 45 Lpm and less than or equal to 200 Lpm. As such, the low inhalation event may not be used at all in some cases.

The pressure measurement readings and/or the computed airflow metrics may also be indicative of the direction of flow through the flow pathway 119 of the inhaler 100. For example, if the pressure measurement readings reflect a negative change in pressure, the readings may be indicative of air flowing out of the mouthpiece 106 via the flow pathway 119. If the pressure measurement readings reflect a positive change in pressure, the readings may be indicative of air flowing into the mouthpiece 106 via the flow pathway 119. Accordingly, the pressure measurement readings and/or airflow metrics may be used to determine whether a subject is exhaling into the mouthpiece 106, which may signal that the subject is not using the device 100 properly.

The inhaler 100 may include a spirometer or similarly operating device to enable measurement of lung function metrics. For example, the inhaler 100 may perform measurements to obtain metrics related to a subject's lung capacity. The spirometer or similarly operating device may measure the volume of air inhaled and/or exhaled by the subject. The spirometer or similarly operating device may use pressure transducers, ultrasound, or a water gauge to detect the changes in the volume of air inhaled and/or exhaled.

The personalized data collected from, or calculated based on, the usage of the inhaler 100 (e.g. pressure metrics, airflow metrics, lung function metrics, dose confirmation information, etc.) may be computed and/or assessed via external devices as well (e.g. partially or entirely). More specifically, the wireless communication circuit 129 in the electronics module 120 may include a transmitter and/or receiver (e.g. a transceiver), as well as additional circuitry. The wireless communication circuit 129 may include, or define, the transmission module 14 of the inhaler 100.

For example, the wireless communication circuit 129 may include a Bluetooth chip set (e.g. a Bluetooth Low Energy chip set), a ZigBee chipset, a Thread chipset, etc. As such, the electronics module 120 may wirelessly provide the personalized data, such as pressure measurements, airflow metrics, lung function metrics, dose confirmation information, and/or other conditions related to usage of the inhaler 100, to an external processing module 34, such as a processing module 34 included in a smart phone 40. The personalized data may be provided in real time to the external device to enable exacerbation risk prediction based on real-time data from the inhaler 100 that indicates time of use, how the inhaler 100 is being used, and personalized data about the subject, such as real-time data related to the subject's lung function and/or medical treatment. The external device may include software for processing the received information and for providing compliance and adherence feedback to the subject via a graphical user interface (GUI). The graphical user interface may be included in, or may define, the user interface 38 included in the system 10.

The airflow metrics may include personalized data that is collected from the inhaler 100 in real-time, such as one or more of an average flow of an inhalation/exhalation, a peak flow of an inhalation/exhalation (e.g. a maximum inhalation received), a volume of an inhalation/exhalation, a time to peak of an inhalation/exhalation, and/or the duration of an inhalation/exhalation. The airflow metrics may also be indicative of the direction of flow through the flow pathway 119. That is, a negative change in pressure may correspond to an inhalation from the mouthpiece 106, while a positive change in pressure may correspond to an exhalation into the mouthpiece 106. When calculating the airflow metrics, the electronics module 120 may be configured to eliminate or minimize any distortions caused by environmental conditions. For example, the electronics module 120 may re-zero to account for changes in atmospheric pressure before or after calculating the airflow metrics. The one or more pressure measurements and/or airflow metrics may be time-stamped and stored in the memory of the electronics module 120.

In addition to the airflow metrics, the inhaler 100, or another computing device, may use the airflow metrics to generate additional personalized data. For example, the controller of the electronics module 120 of the inhaler 100 may translate the airflow metrics into other metrics that indicate the subject's lung function and/or lung health that are understood to medical practitioners, such as peak inspiratory flow metrics, peak expiratory flow metrics, and/or forced expiratory volume in 1 second (FEV1), for example. The electronics module 120 of the inhaler may determine a measure of the subject's lung function and/or lung health using a mathematical model such as a regression model. The mathematical model may identify a correlation between the total volume of an inhalation and FEV1. The mathematical model may identify a correlation between peak inspiratory flow and FEV1. The mathematical model may identify a correlation between the total volume of an inhalation and peak expiratory flow. The mathematical model may identify a correlation between peak inspiratory flow and peak expiratory flow.

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a particular battery capacity that may affect the life of the battery 126. As will be further discussed below, the distribution of power from the battery 126 to the one or more components of the PCB 122 may be managed to ensure the battery 126 can power the electronics module 120 over the useful life of the inhaler 100 and/or the medication contained therein.

In a connected state, the communication circuit and memory may be powered on and the electronics module 120 may be "paired" with an external device, such as a smart phone. The controller may retrieve data from the memory and wirelessly transmit the data to the external device. The controller may retrieve and transmit the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

The data stored in the memory of the electronics module 120 (e.g. the signals generated by the switch 130, the pressure measurement readings taken by the sensory system 128 and/or the airflow metrics computed by the controller of the PCB 122) may be transmitted to an external device, which may process and analyze the data to determine the usage parameters associated with the inhaler 100. Further, a mobile application residing on the mobile device may generate feedback for the user based on data received from the electronics module 120. For example, the mobile application may generate daily, weekly, or monthly report, provide confirmation of error events or notifications, provide instructive feedback to the subject, and/or the like.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Embodiments. Below are non-limiting examples of various embodiments that are discussed herein.

1. A system comprising:
   at least one first inhaler configured to deliver a first medicament to a subject, each of the at least one first inhaler comprising:
   a first use determination system configured to determine a first value of a usage parameter relating to use of the respective first inhaler; and
   a first transmission module configured to encrypt first data based on the first value, and transmit the encrypted first data;
   at least one second inhaler configured to deliver a second medicament to the subject, the second medicament being different from the first medicament, each of the at least one second inhaler comprising:
   a second use determination system configured to determine a second value of a usage parameter relating to use of the respective second inhaler; and
   a second transmission module configured to encrypt second data based on the second value, and transmit the encrypted second data;
   a user interface; and
   a processing module configured to:
   receive the first encrypted data and the second encrypted data;
   distinguish between the first encrypted data and the second encrypted data;
   determine first usage information relating to the first medicament from the distinguished first encrypted data;
   determine second usage information relating to the second medicament from the distinguished second encrypted data; and
   control the user interface to communicate the first and second usage information.

2. The system according to claim 1, further comprising at least one third inhaler configured to deliver a third medicament to the subject which is different from the first and second medicaments, each of the at least one third inhaler comprising:
   a third use determination system configured to determine a third value of a usage parameter relating to use of the respective third inhaler; and
   a third transmission module configured to encrypt third data based on the third value, and transmit the encrypted third data, wherein the processing module is configured to:
   receive the third encrypted data;
   distinguish the third encrypted data from the encrypted data transmitted from the respective transmission modules included in the other inhalers included in the system;
   determine third usage information relating to the third medicament from the distinguished third encrypted data; and
   control the user interface to communicate the first, second, and third usage information.

3. The system according to claim 1 or claim 2, wherein a first identifier, provided with the first inhaler, is assigned to the first medicament, and a second identifier, provided with the second inhaler, is assigned to the second medicament, wherein the processing module is configured to receive the respective identifiers, and use the respective identifiers to distinguish between the first encrypted data and the second encrypted data.

4. The system according to claim 3 as according to claim 2, wherein a third identifier, provided with the third inhaler, is assigned to the third medicament, wherein the processing module is configured to receive the third identifier, and use the first, second, and third identifiers to distinguish the third encrypted data from the first and second encrypted data.

5. The system according to claim 3 or claim 4, wherein the respective identifier received by the processing module further denotes a dose strength of the respective medicament which the respective inhaler is configured to deliver, and optionally a total number of doses which the respective inhaler contains as supplied to the subject, and wherein the processing module is configured to control the user interface to issue a notification based on the respective usage information and the respective dose strength.

6. The system according to any of claims 1 to 5, wherein the at least one first inhaler comprises two or more first inhalers and/or wherein the at least one second inhaler comprises two or more second inhalers.

7. The system according to any of claims 1 to 6, wherein the usage parameter comprises a use of the respective inhaler; optionally wherein the use determination system comprises a sensor for detecting inhalation of the respective medicament performed by the subject and/or a mechanical switch configured to be actuated prior to, during, or after use of the respective inhaler.

8. The system according to any of claims 1 to 7, wherein the usage parameter comprises a parameter relating to airflow during inhalation of the respective medicament performed by the subject.

9. The system according to claim 8, wherein the use determination system comprises a sensor for sensing the parameter; optionally wherein the parameter is at least one of a peak inhalation flow, an inhalation volume, a time to peak inhalation flow, and an inhalation duration.

10. The system according to claim 9 as according to claim 7, wherein the sensor for sensing the parameter is the same as or different from the sensor for detecting inhalation of the respective medicament performed by the subject.

11. The system according to any of claims 1 to 10, wherein a clock module is included in each of the respective inhalers for assigning a time to said usage parameter of the respective inhaler, wherein the processing module is configured to synchronize the clock modules of the respective inhalers; optionally wherein said assigned time is included in the usage information for the respective medicaments.

12. The system according to claim 11, wherein the processing module comprises a further clock module, the clock modules of each of the respective inhalers being synchronized according to the time provided by the further clock module; optionally wherein the further clock module is configured to provide the time of the time zone in which the processing module and the respective inhalers are situated.

13. The system according to any of claims 1 to 12, wherein the first medicament is a rescue medicament for use by the subject as needed, and the second medicament is a maintenance medicament.

14. The system according to any of claims 1 to 13, wherein the first medicament is albuterol, and the second medicament is salmeterol combined with fluticasone, budesonide combined with formoterol, or beclomethasone.

15. The system according to any of claims 1 to 14, wherein the user interface is at least partly defined by a first user interface of a user device; optionally wherein the user device is at least one selected from a personal computer, a tablet computer, and a smart phone.

16. The system according to claim 15, wherein the processing module is at least partly included in a first processing module included in the user device.

17. A method comprising:
receiving first encrypted data from a first transmission module of a first inhaler configured to deliver a first medicament to a subject, the first encrypted data being based on a first value of a usage parameter relating to use of the first inhaler;
receiving second encrypted data from a second transmission module included in a second inhaler configured to deliver a second medicament to the subject, the second encrypted data being based on a second value of a usage parameter relating to use of the second inhaler, wherein the second medicament is different from the first medicament;
distinguishing between the first encrypted data and the second encrypted data;
determining first usage information relating to the first medicament from the distinguished first encrypted data;
determining second usage information relating to the second medicament from the distinguished second encrypted data; and
controlling a user interface to communicate the first and second usage information.

18. The method according to claim 17, wherein said receiving the first encrypted data comprises receiving the first encrypted data from each respective first transmission module of a plurality of first inhalers, each of said plurality of first inhalers being configured to deliver the first medicament, and/or wherein said receiving the second encrypted data comprises receiving the second encrypted data from each respective second transmission module of a plurality of second inhalers, each of said plurality of second inhalers being configured to deliver the second medicament.

19. The method according to claim 17 or claim 18, further comprising:
receiving third encrypted data from a third transmission module included in a third inhaler configured to deliver a third medicament which is different from the first and second medicaments;
distinguishing the third encrypted data from the first encrypted data and the second encrypted data;
determining third usage information relating to the third medicament from the distinguished third encrypted data; and
controlling the user interface to communicate the third usage information.

20. The method according to claim 19, wherein said receiving the third encrypted data comprises receiving the third encrypted data from each respective third transmission module of a plurality of third inhalers, each of said plurality of third inhalers being configured to deliver the third medicament.

21. The method according to any of claims 17 to 20, comprising:
receiving a first identifier, the first identifier being assigned to the first medicament; and receiving a second identifier, the second identifier being assigned to the second medicament, wherein the distinguishing between the first encrypted data and the second encrypted data comprises using the first and second identifiers.

22. The method according to claim 21 as according to claim 19 or claim 20, comprising receiving a third identifier, the third identifier being assigned to the third medicament, wherein the distinguishing the third encrypted data from the first encrypted data and the second encrypted data comprises using the first, second, and third identifiers.

23. The method according to any of claims 17 to 22, wherein a clock module is included in each of the respective inhalers for assigning a time to said usage parameter of the respective inhaler, wherein the method further comprises synchronizing the clock modules of the respective inhalers; optionally wherein said assigned time is included in the usage information for the respective medicaments.

24. The method according to claim 23, wherein the synchronizing comprises synchronizing each of the respective clock modules with the time of the time zone in which the respective inhalers are situated.

25. A computer program comprising computer program code which is adapted, when said computer program is run on a computer, to implement the method of any of claims 17 to 24.

What is claimed is:

1. A system comprising:
   a first inhaler configured to deliver a first medicament to a subject, the first inhaler comprising:
   a sensor for detecting inhalation of the first medicament performed by the subject;
   a processor configured to determine a first usage parameter relating to use of the first inhaler, and encrypt first data based on the first usage parameter; and
   a transmitter configured to transmit the encrypted first data; and
   a second inhaler configured to deliver a second medicament to the subject, the second medicament being different from the first medicament, the second inhaler comprising:
   a sensor for detecting inhalation of the second medicament performed by the subject;
   a processor configured to determine a second usage parameter relating to use of the second inhaler, and encrypt second data based on the second usage parameter; and
   a transmitter configured to transmit the encrypted second data;
   a non-transitory computer-readable storage medium residing on an external device, wherein the non-transitory computer-readable storage medium comprises computer-executable instructions that, when executed by a processor of the external device cause the processor of the external device to:
   receive the first encrypted data and the second encrypted data;
   distinguish between the first encrypted data and the second encrypted data;
   determine first usage information from the distinguished first encrypted data;
   determine second usage information from the distinguished second encrypted data;
   determine that the first usage information indicates a first instance of a use error, and that the second usage information indicates a second instance of the use error; and
   generate a user interface to provide a notification of the use error based on an aggregated total of the first instance of the use error indicated by the first usage information and the second instance of the use error indicated by the second usage information exceeding a predetermined number.

2. The system of claim 1, wherein the use error comprises a low inhalation event or a no inhalation event.

3. The system of claim 1, wherein the use error comprises an exhalation-based use error.

4. The system of claim 1, wherein the use error comprises an excessive inhalation event.

5. The system of claim 1, wherein the use error comprises an indication that a mouthpiece cover of the first inhaler or a mouthpiece cover of the second inhaler was left open for more than a predetermined time period.

6. The system of claim 1, wherein the use error comprises an indication that multiple inhalations were recorded during a single use of the first inhaler or the second inhaler.

7. The system of claim 1, wherein a first identifier, associated with the first inhaler, is assigned to the first medicament, and a second identifier, associated with the second inhaler, is assigned to the second medicament; and
   wherein the non-transitory computer-readable storage medium comprises computer-executable instructions that, when executed by the processor of the external device cause the processor of the external device to receive the respective identifiers, and use the respective identifiers to distinguish between the first encrypted data and the second encrypted data.

8. The system of claim 7, wherein the respective identifiers received by the external device further denotes a dose strength of the respective medicament which the respective inhaler is configured to deliver, and denotes a total number of doses which the respective inhaler contains as supplied to the subject; and
   wherein non-transitory computer-readable storage medium comprises computer-executable instructions that, when executed by the processor of the external device cause the processor of the external device to control the user interface to issue a notification based on the respective usage information and the respective dose strength of the first and second inhalers.

9. The system of claim 1, wherein the non-transitory computer-readable storage medium comprises computer-executable instructions that, when executed by the processor of the external device cause the processor of the external device to:
   control the user interface to communicate the first usage information and the second usage information in a consolidated display, wherein the first usage information comprises a classification of the use of the first inhaler as a low inhalation, a no inhalation event, an exhalation-based use error, or an excessive inhalation event, and wherein the second usage information comprises a classification of the use of the second inhaler as a low inhalation, a no inhalation event, an exhalation-based use error, or an excessive inhalation event.

10. The system of claim 1, wherein the processor of the first inhaler further is configured to assign a time to said usage parameter of the first inhaler, and the processor of the second inhaler is configured to assign a time to said usage parameter of the second inhaler; and
    wherein the computer-readable storage medium comprises non-transitory computer-executable instructions that, when executed by the processor of the external device cause the processor of the external device to synchronize the assigned times of the usage parameters of the respective inhalers.

11. The system of claim 10, wherein the non-transitory computer-readable storage medium comprises computer-executable instructions that, when executed by the processor of the external device cause the processor of the external device to provide, to the respective inhalers, a time of a time zone in which the external device and the respective inhalers are situated.

12. A method comprising:
receiving the first encrypted data and the second encrypted data, wherein the first encrypted data is based on a first usage parameter relating to a sensed inhalation of a first medicament performed by a subject via a first inhaler, wherein the second encrypted data is based on a second usage parameter relating to a sensed inhalation of a second medicament performed by the subject via a second inhaler;
distinguishing between the first encrypted data and the second encrypted data;
determining first usage information from the distinguished first encrypted data;
determining second usage information from the distinguished second encrypted data;
determining that the first usage information indicates a first instance of a use error, and that the second usage instance of the information indicates a second use error; and
generating a user interface to provide a notification of the use error based on an aggregated total of the first instance of the use error indicated by the first usage information and the second instance of the use error indicated by the second usage information exceeding a predetermined number.

13. The method of claim 12, wherein the use error comprises a low inhalation event or a no inhalation event.

14. The method of claim 12, wherein the use error comprises an exhalation-based use error.

15. The method of claim 12, wherein the use error comprises an excessive inhalation event.

16. The method of claim 12, wherein the use error comprises an indication that a mouthpiece cover of the first inhaler or a mouthpiece cover of the second inhaler was left open for more than a predetermined time period.

17. The method of claim 12, wherein the use error comprises an indication that multiple inhalations were recorded during a single use of the first inhaler or the second inhaler.

18. A non-transitory computer-readable storage medium residing on an external device, wherein the non-transitory computer-readable storage medium comprises computer-executable instructions that, when executed by a processor of the external device cause the processor of the external device to:
receive the first encrypted data and the second encrypted data, wherein the first encrypted data is based on a first usage parameter relating to a sensed inhalation of a first medicament performed by a subject via a first inhaler, wherein the second encrypted data is based on a second usage parameter relating to a sensed inhalation of a second medicament performed by the subject via a second inhaler;
distinguish between the first encrypted data and the second encrypted data;
determine first usage information from the distinguished first encrypted data;
determine second usage information from the distinguished second encrypted data;
determine that the first usage information indicates a first instance of a use error, and that the second usage instance of the information indicates a second use error; and
generate a user interface to provide a notification of the use error based on an aggregated total of the first instance of the use error indicated by the first usage information and the second instance of the use error indicated by the second usage information exceeding a predetermined number.

19. The non-transitory computer-readable storage medium of claim 18, wherein the use error comprises a low inhalation event or a no inhalation event.

20. The non-transitory computer-readable storage medium of claim 18, wherein the use error comprises an exhalation-based use error.

\* \* \* \* \*